(12) United States Patent
Vigna et al.

(10) Patent No.: US 10,940,307 B2
(45) Date of Patent: Mar. 9, 2021

(54) STERILE CONNECTION/DISCONNECTION COUPLING AND METHOD

(71) Applicant: EMD Millipore Corporation, Burlington, MA (US)

(72) Inventors: James Vigna, Burlington, MA (US); Joseph Muldoon, Burlington, MA (US); John Cieciuch, Burlington, MA (US); Robert Langlois, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 16/895,521

(22) Filed: Jun. 8, 2020

(65) Prior Publication Data

US 2020/0297990 A1    Sep. 24, 2020

Related U.S. Application Data

(60) Continuation of application No. 15/867,915, filed on Jan. 11, 2018, now Pat. No. 10,675,454, which is a
(Continued)

(51) Int. Cl.
*A61M 39/18*    (2006.01)
*F16L 37/36*    (2006.01)
(Continued)

(52) U.S. Cl.
CPC ............ *A61M 39/18* (2013.01); *A61M 39/26* (2013.01); *F16L 37/36* (2013.01); *F16L 37/367* (2013.01); *F16L 55/07* (2013.01); *F16L 2201/44* (2013.01)

(58) Field of Classification Search
CPC ...... A61M 39/18; A61M 39/26; F16L 37/367; F16L 37/36; F16L 2201/44
See application file for complete search history.

(56) References Cited

U.S. PATENT DOCUMENTS

| 263,330 A | 8/1882 | Franklin |
|---|---|---|
| 950,263 A | 2/1910 | Harpster |

(Continued)

FOREIGN PATENT DOCUMENTS

| AU | 2011211445 A1 | 9/2011 |
|---|---|---|
| CN | 101526174 A | 9/2009 |

(Continued)

OTHER PUBLICATIONS

International Search Report and Written Opinion dated Aug. 21, 2014 in corresponding PCT application No. PCT/US2014/031829.
(Continued)

*Primary Examiner* — David Colon-Morales
(74) *Attorney, Agent, or Firm* — Nields, Lemack & Frame, LLC

(57) ABSTRACT

Fluid transfer device and method that allows for sterile wet connections, allows the connection to be reversed, and allows the connection to be reconnected, while leaving the connectors sterile and reusable under pressure. In certain embodiments, the device includes a first member and a second member, the latter adapted to receive the former in locking engagement upon actuation of the device to create fluid communication between the two in a sterile manner. Each of the members include a door that when opened, allows the first member to be linearly displaced into the second member to allow fluid to be transferred. When fluid transfer is complete, the first member can be retracted from the second member, and the doors closed.

16 Claims, 33 Drawing Sheets

Related U.S. Application Data division of application No. 14/773,426, filed as application No. PCT/US2014/031829 on Mar. 26, 2014, now Pat. No. 9,901,729.

(60) Provisional application No. 61/806,442, filed on Mar. 29, 2013.

(51) Int. Cl.
*F16L 37/367* (2006.01)
*F16L 55/07* (2006.01)
*A61M 39/26* (2006.01)

(56) References Cited

U.S. PATENT DOCUMENTS

| | | | |
|---|---|---|---|
| 2,073,048 A | 3/1937 | Clark | |
| 2,317,827 A | 4/1943 | Townhill | |
| 2,333,496 A | 11/1943 | Townhill et al. | |
| 2,399,516 A | 4/1946 | Snyder | |
| 2,399,525 A | 4/1946 | Waag | |
| 2,403,620 A | 7/1946 | Snyder et al. | |
| 2,687,903 A | 8/1954 | Zeeb | |
| 2,709,090 A | 5/1955 | Zeeb | |
| 2,749,146 A | 6/1956 | Gumbert et al. | |
| 2,757,941 A | 8/1956 | Zeeb | |
| 2,779,608 A | 1/1957 | Abbey | |
| 2,823,887 A | 2/1958 | Osinski | |
| 2,828,146 A | 3/1958 | Abbey | |
| 3,106,223 A | 10/1963 | Cooper | |
| 3,357,452 A | 12/1967 | Larkin et al. | |
| 3,909,910 A * | 10/1975 | Rowe | |
| 4,019,512 A | 4/1977 | Tenczar | |
| 4,022,205 A | 5/1977 | Tenczar | |
| 4,089,506 A | 5/1978 | Blake | |
| 4,253,684 A | 3/1981 | Feder | |
| 4,271,865 A | 6/1981 | Galloway et al. | |
| 4,275,763 A | 6/1981 | Fahrig | |
| 4,306,705 A | 12/1981 | Svensson | |
| 4,334,551 A | 6/1982 | Pfister | |
| 4,418,945 A * | 12/1983 | Kellogg | |
| 4,456,026 A | 6/1984 | Kantor | |
| 4,509,554 A | 4/1985 | Failla | |
| 4,564,054 A | 1/1986 | Gustavsson | |
| 4,576,199 A | 3/1986 | Svensson et al. | |
| 4,610,469 A | 9/1986 | Wolff-Mooij | |
| 4,942,901 A | 7/1990 | Vescovini | |
| 4,989,638 A | 2/1991 | Tervo | |
| 5,009,252 A | 4/1991 | Faughn | |
| 5,039,063 A | 8/1991 | Louch et al. | |
| 5,092,363 A | 3/1992 | Vanderjagt | |
| 5,165,439 A | 11/1992 | Krynicki | |
| 5,492,147 A | 2/1996 | Challender et al. | |
| 5,662,141 A | 9/1997 | Arosio | |
| 5,738,143 A | 4/1998 | Faughn | |
| 5,884,648 A | 3/1999 | Savage | |
| 6,077,259 A | 6/2000 | Caizza et al. | |
| 6,394,132 B1 | 5/2002 | Walcome | |
| 7,137,974 B2 | 11/2006 | Almasian et al. | |
| 7,350,535 B2 | 4/2008 | Liepold et al. | |
| 7,396,051 B2 | 7/2008 | Baldwin et al. | |
| 7,678,096 B2 * | 3/2010 | Biddel | A61M 39/16 604/403 |
| 7,708,025 B2 | 5/2010 | Johnson | |
| 7,918,243 B2 | 4/2011 | Diodati et al. | |
| 7,922,211 B2 | 4/2011 | Arthun et al. | |
| 8,671,964 B2 | 3/2014 | Py | |
| 8,746,278 B2 | 6/2014 | Py | |
| 9,901,729 B2 | 2/2018 | Vigna et al. | |
| 10,675,454 B2 | 6/2020 | Vigna et al. | |
| 2003/0030272 A1 | 2/2003 | Johnson et al. | |
| 2003/0032940 A1 | 2/2003 | Doyle | |
| 2005/0016620 A1 | 1/2005 | Proulx et al. | |
| 2009/0229671 A1 | 9/2009 | Hartnett et al. | |
| 2009/0232586 A1 | 9/2009 | Diodati | |
| 2012/0042971 A1 | 2/2012 | Py | |
| 2014/0345748 A1 | 11/2014 | Rogers et al. | |
| 2016/0022979 A1 | 1/2016 | Vigna et al. | |
| 2018/0133453 A1 | 5/2018 | Vigna et al. | |
| 2018/0161568 A1 | 6/2018 | Banco et al. | |

FOREIGN PATENT DOCUMENTS

| | | |
|---|---|---|
| CN | 201916514 U | 8/2011 |
| CN | 103477201 A | 12/2013 |
| EP | 0116986 A1 | 8/1984 |
| EP | 0715860 A1 | 6/1996 |
| FR | 2958365 A1 | 10/2011 |
| JP | 2000-107300 A | 4/2000 |
| JP | 2005-315338 A | 11/2005 |
| JP | 2009-530561 A | 8/2009 |
| WO | 98/50105 A1 | 11/1998 |
| WO | 03/090843 A1 | 11/2003 |
| WO | 2004/082756 A1 | 9/2004 |
| WO | 2007/107500 A1 | 9/2007 |
| WO | 2010/142385 A1 | 12/2010 |
| WO | 2012/114105 A1 | 8/2012 |

OTHER PUBLICATIONS

International Preliminary Report on Patentability dated Oct. 8, 2015 in corresponding PCT application No. PCT/US2014/031829.
European communication dated Oct. 26, 2016 in corresponding European patent application No. 14774870.1
Chinese communication, with English translation, dated Aug. 31, 2016 in corresponding Chinese patent application No. 201480019424.0.
Japanese communication, with English translation, dated Nov. 11, 2016 in corresponding Japanese patent application No. 2016-505544.
Japanese communication, with English translation, dated Sep. 5, 2017 in corresponding Japanese patent application No. 2016-505544.
Chinese communication, with English translation, dated Aug. 30, 2019 in corresponding Chinese patent application No. 201810448671.2.

* cited by examiner

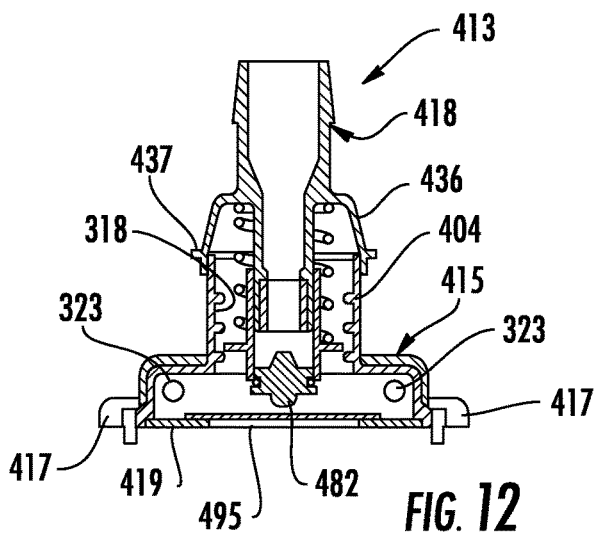
FIG. 12
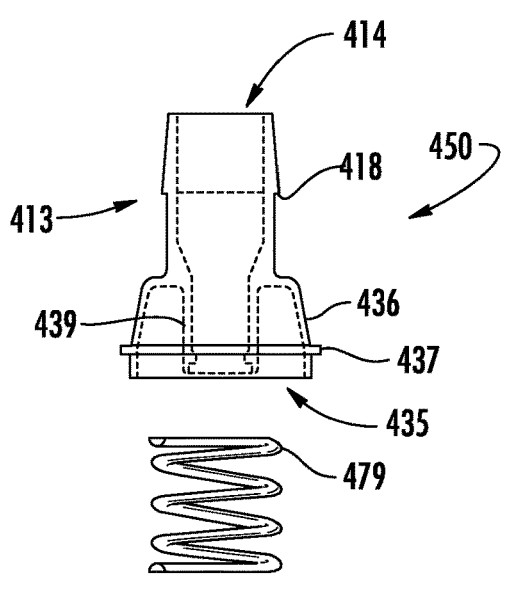
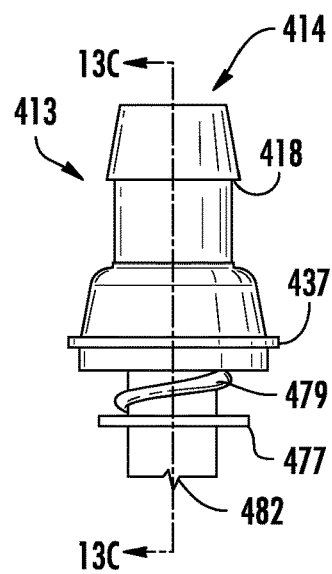
FIG. 13B
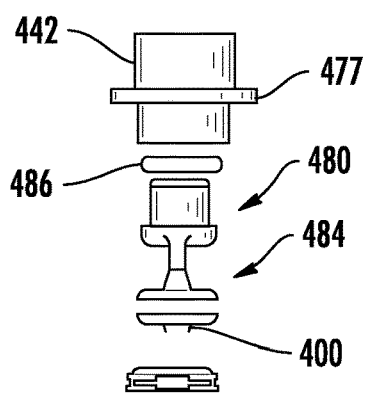
FIG. 13A
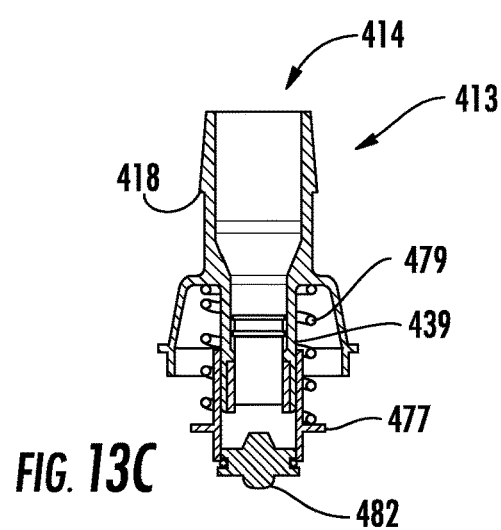
FIG. 13C

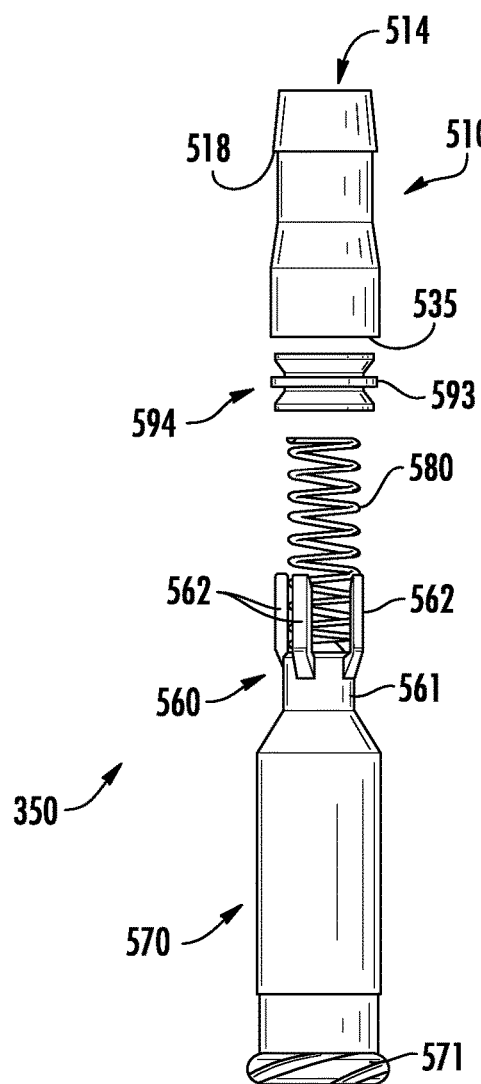
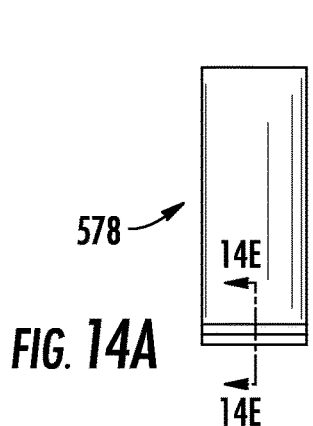
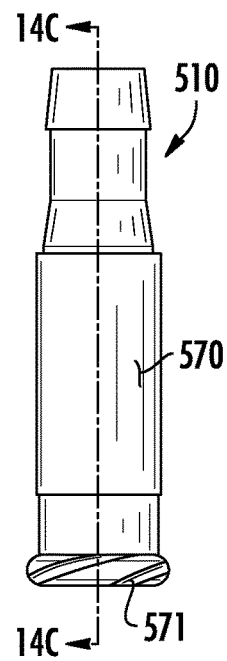
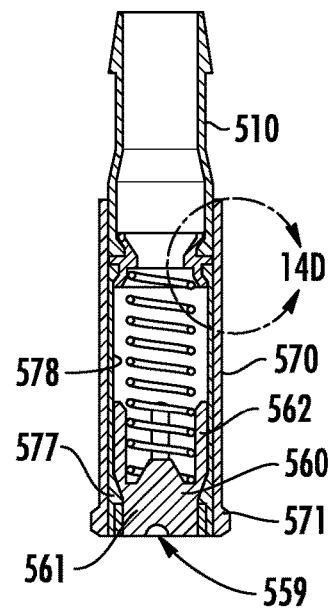
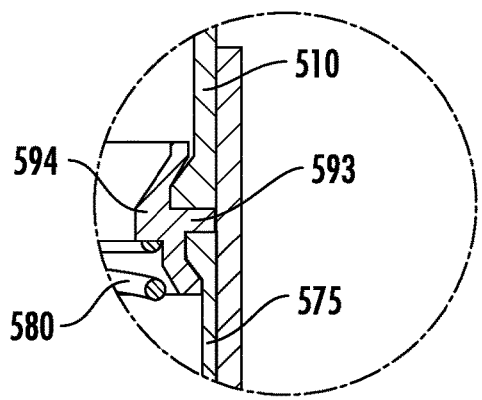
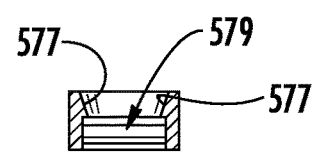
FIG. 14A
FIG. 14B
FIG. 14C
FIG. 14D
FIG. 14E

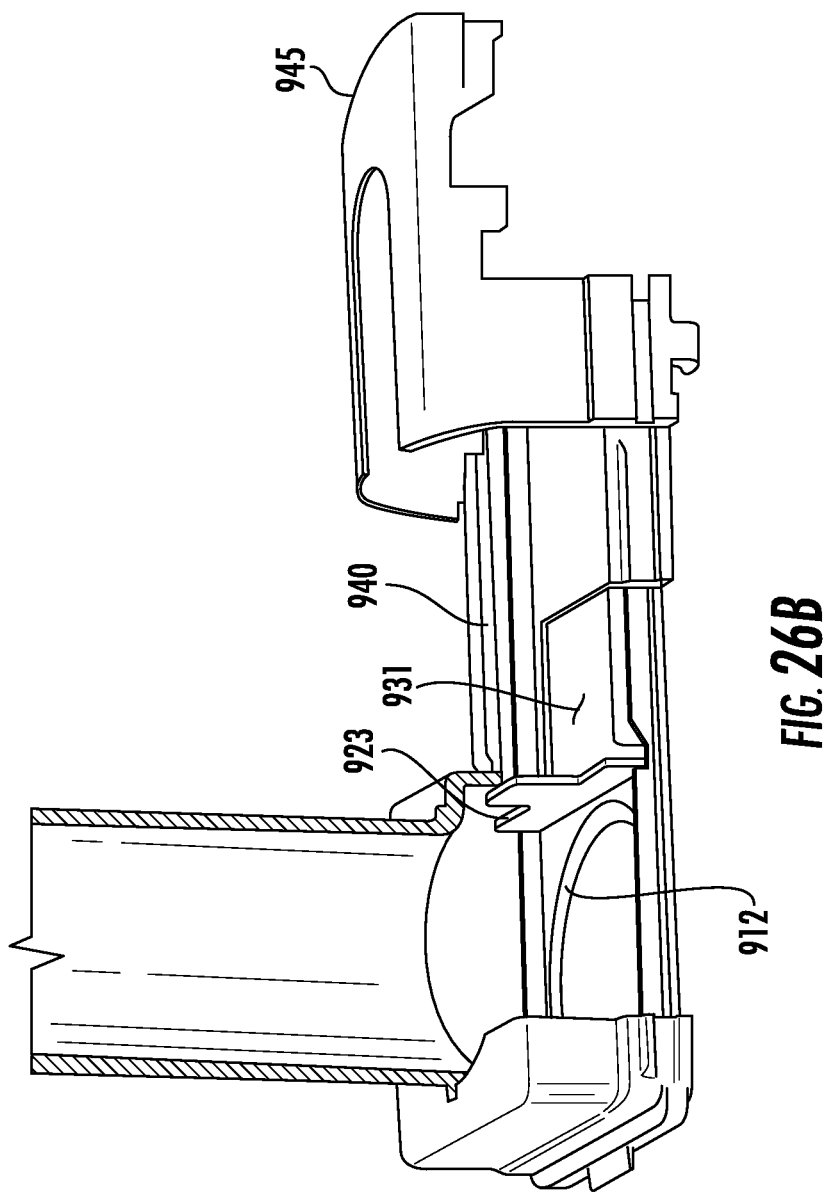

STERILE CONNECTION/DISCONNECTION COUPLING AND METHOD

This application is a continuation of U.S. patent application Ser. No. 15/867,915 filed Jan. 11, 2018, which is a divisional of U.S. patent application Ser. No. 14/773,426 filed Sep. 8, 2015 (now U.S. Pat. No. 9,901,729 Issued Feb. 27, 2018), which claims priority of US Provisional Application Ser. No. 61/806,442 filed Mar. 29, 2013, the disclosures of which are hereby incorporated by reference. U.S. patent application Ser. No. 14/773,426 filed Sep. 8, 2015 is a 371 of PCT/US2014/031829 filed Mar. 26, 2014.

BACKGROUND

The embodiments disclosed herein relate to the transfer of media, such as liquids, into or from a container or the like. For example, the embodiments disclosed herein relate to a fluid transfer device in the form of a connector or valve, enabling good sterile fluid transfer between two systems.

When conducting complex and/or delicate fluid processes within a "closed" fluid system, it is often necessary to connect or link unit operations of the manufacturing process or to monitor the progress of the process it is often desirable to transfer the fluid without disturbing the process, such as may occur upon "opening" the receptacle or unit operation. For example, in the study and/or manufacture of biochemical products (e.g., biopharmaceuticals), biochemical fluid is often contained in an aseptically "closed" fermenting tank, bioreactor, or like fluid receptacle, wherein the fluid is processed over comparatively long periods of time, under diverse and changing chemical and environmental conditions. By withdrawing and analyzing samples of the fluid intermittently in the course of the process, one can learn more about the progress of the process, and if called for, take prophylactic measures to change the outcome thereof. There also exists a need to connect multiple unit operations together or draw from or add to multiple vessels into a common flow conduit in a sterile manner without "opening" the vessel or flow conduit and disrupting the process.

Similar issues arise also in instances wherein fluid is conducted through a conduit, or a pipe, or other like fluid receptacle. Sampling of said fluid is often difficult because in many industrial systems, said receptacles are not easily opened or disassembled to allow one to withdraw fluid samples, especially in a sterile manner. While several fluid sampling techniques are known, certain technical issues can be noted. For example, certain integrated fluid sampling fixtures comprise stainless steel valves and piping which, for biopharmaceutical applications, often require laborious steam sterilization and cleaning prior to use. Other fluid sampling devices are difficult to integrate into extant fluid processing systems, for example, by requiring the installation of custom-fitted ports onto a host fluid receptacle. Still other devices, although adapted for use in standard industrial ports, are complex and costly instruments comprising valves, inlets, outlets, seals, needles, and other components, all precisely arranged, but capable of only a single aseptic sample per sterilization cycle. Finally, the majority of fluid sampling devices—as is the case in many of those already mentioned—require in their operation the piercing of a septum using a hypodermic needle There is a need for the introduction or removal of materials from the process stream in order to add components of the product, such as media or buffers to a bioreactor; withdraw samples from the process stream to check for microbial contamination, quality control, process control, etc; conduct unit operations such as mixing, filtration, cell culture, etc., and to fill the product into its final container such as vials, syringes, sealed boxes, bottles, single use storage containers such as film bags, single use mix bags/mixers, and the like.

In light of the above, a need exists for a fluid transfer device that can provide a sterile wet connection, under pressure, provide a dripless disconnection, and completely reverse the connection leaving the flow path sterile and reusable.

SUMMARY

Embodiments disclosed herein provide a fluid transfer device that allows for wet connections under pressure, allows the connection to be reversed, and allows the connection to be reconnected, while leaving the connectors sterile and reusable. In certain embodiments, the device is in the form of a connector or valve. In certain embodiments, the device includes a first member or housing and a second member or housing, one adapted to receive the other in locking engagement upon actuation of the device to create fluid communication between the two in a sterile manner. Each of the members or housings includes a door that when opened, allows a valve sleeve of one member to be displaced into the other member to allow fluid to be transferred. When fluid transfer is complete, the valve sleeve can be retracted, and the doors closed.

In accordance with certain embodiments, disclosed is a fluid transfer device comprising a first member or housing, the first member or housing comprising a first body member having a port and a grooved surface, and a first base having an outlet. The device also includes a second member or housing, the second member or housing comprising a second body member, a second member valve sleeve member having at least one thread configured to be engaged in the grooved surface of the first body member, and a second inner body having an inlet. The second member valve sleeve member is linearly displaceable into and out of the first body member to create (and eliminate) fluid communication between the inlet and the outlet.

Drip-Free Connection and Disconnection are Achieved.

In certain embodiments, the fluid transfer device includes first and second members or housings, which can be engaged or coupled and locked together. The act or acts of engagement or coupling, and locking of the two members or housings, also creates sterile fluid communication between the two members or housings, and thus between valve members carried by the two members or housings. In certain embodiments, the act or acts of engaging or coupling, and locking the two members or housings creates sterile fluid communication by actuating one or more doors within the device to open positions. In certain embodiments, the act or acts of engaging and coupling, and locking the two members or housings is carried out by relative movement of one member or housing with respect to the other. In certain embodiments, the relative movement includes rotational movement. In certain embodiments, the rotational movement includes rotating the first and second members or housings in opposite directions. In certain embodiments, the relative movement includes linear movement. In certain embodiments, the linear movement includes moving the first and second members or housings in the same direction.

In certain embodiments, once the members are engaged or coupled, locked, and fluid communication is achieved, relative displacement of a valve member carried by one of the members or housings into a valve member carried by the other member or housing is effectuated, such as by applying a rotational and/or axial force to one of the valve members.

Suitable materials of construction include materials capable of withstanding the conditions typically encountered by such devices, including those of sterilization. Suitable materials include but are not limited to plastic, stainless steel and aluminum. Suitable plastic materials may include but are not limited to polysulfone, glass filled polysulfone, polyphenylene sulfide, glass filled polyphenylene sulfide, polyphenyl sulfone and glass filled polyphenyl sulfone are all acceptable materials due to their biocompatibility, chemical, heat and creep resistance. The plastic components of said connector may be formed by machining or molding. The seals used in the embodiments disclosed herein can be made of but not limited to silicone, rubber, including natural and synthetic rubbers, thermoplastic elastomers, polyolefins, PTFE, thermoplastic perfluoropolymer resins, urethanes, EPDM rubber, PDDF resins etc. Fluids to be transferred include liquids and gases.

BRIEF DESCRIPTION OF THE DRAWINGS

FIG. 12 is a cross-sectional view of a portion of the first alternative embodiment of a fluid transfer device;

FIG. 13A is an exploded view of a first valve member in accordance with certain embodiments;

FIG. 13B is a side view of the valve member of FIG. 13A;

FIG. 13C is a cross-sectional view of the valve member taken along line A-A of FIG. 13B;

FIG. 14A is an exploded view of a second valve member in accordance with certain embodiments;

FIG. 14B is a side view of the valve member of FIG. 14A;

FIG. 14C is a cross-sectional view of the valve member taken along line B-B of FIG. 14B;

FIG. 14D is a cross-sectional view of section C of FIG. 14C;

FIG. 14E is a cross-sectional view along line D-D of FIG. 14A.

FIG. 26B is another exploded view of the alternative door assembly of FIG. 26 shown partially assembled.

DETAILED DESCRIPTION

Figure 1:
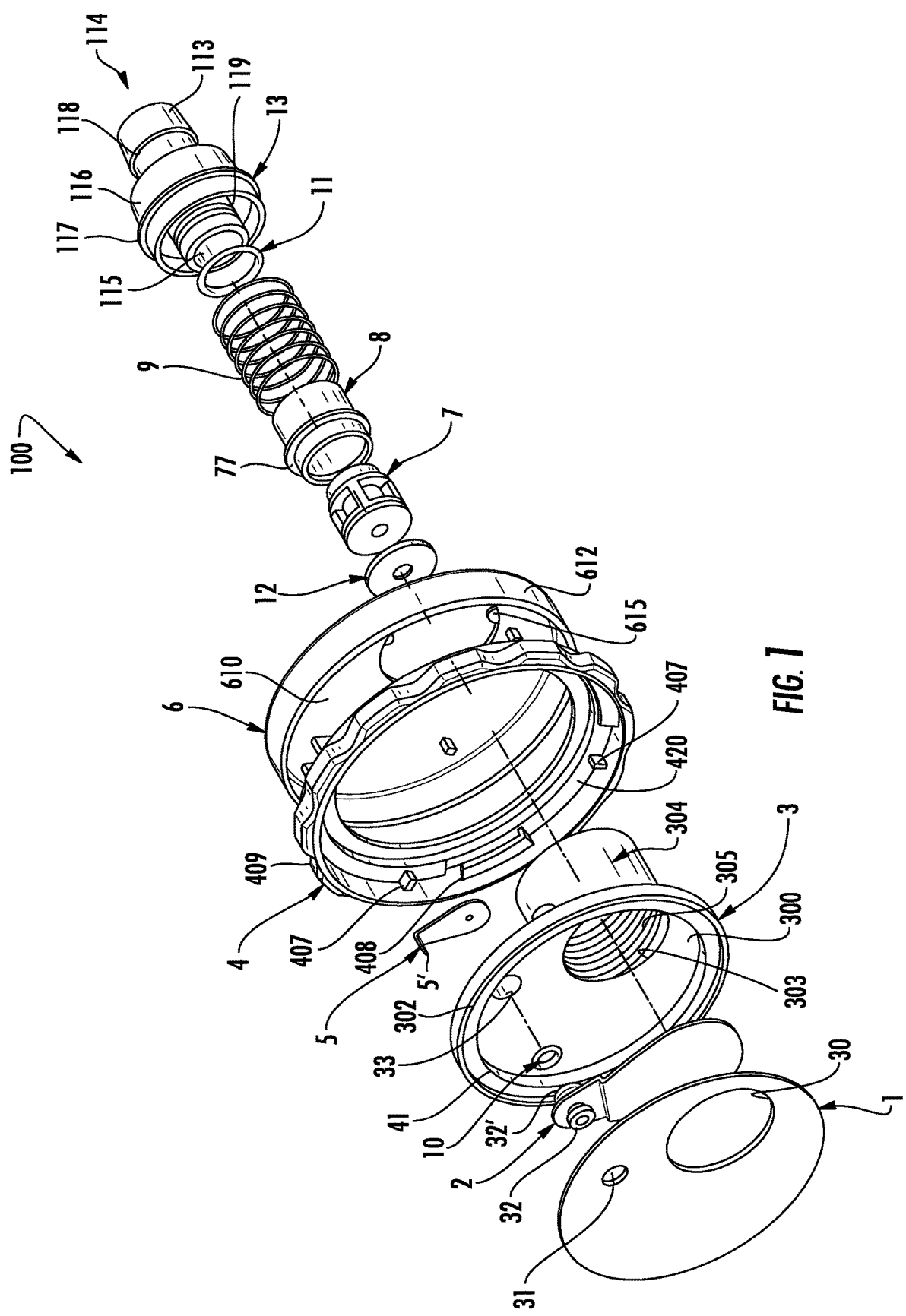
FIG. 1 is a perspective exploded view of a first member of the device in accordance with certain embodiments.

Turning first to FIGS. 1-4, there is shown a first member or housing 100 of the fluid transfer device in accordance with certain embodiments, comprising a first sterility housing plate 1 having a port 30, which is preferably circular, that may be closed or blocked by a movable door 2. Door 2 includes an axially extending shaft member 32 that fits into aperture 31 on first sterility housing plate 1 and about which the door 2 is pivotable to block or unblock the port 30. The door 2, when opened, can be moved inside an isolated pocket (not shown) within the device to protect the internal chamber of the device from anything that may be on the external face of the door.

Figure 2:
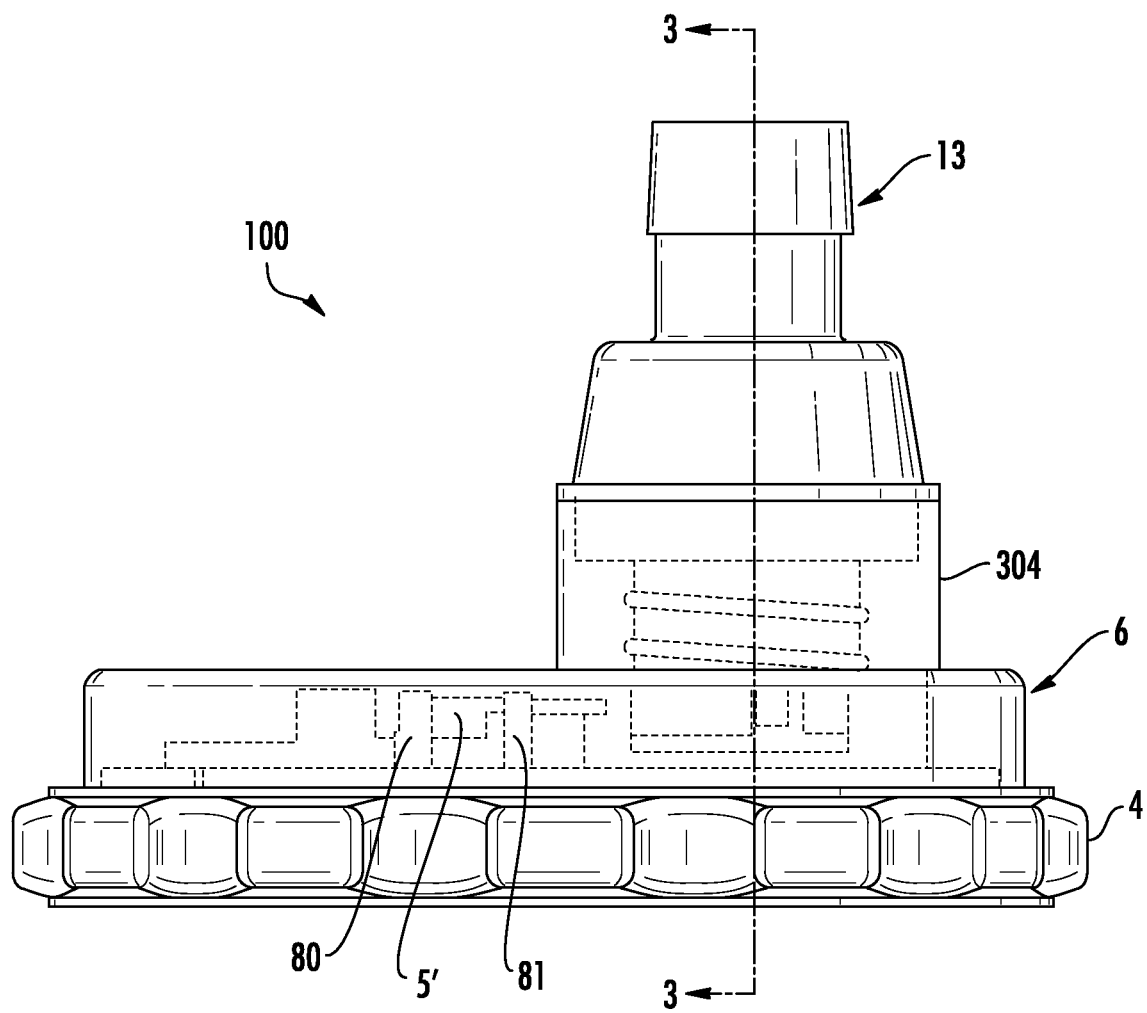
FIG. 2 is a side view of a first member of the device in an assembled condition in accordance with certain embodiments.
Figure 3:
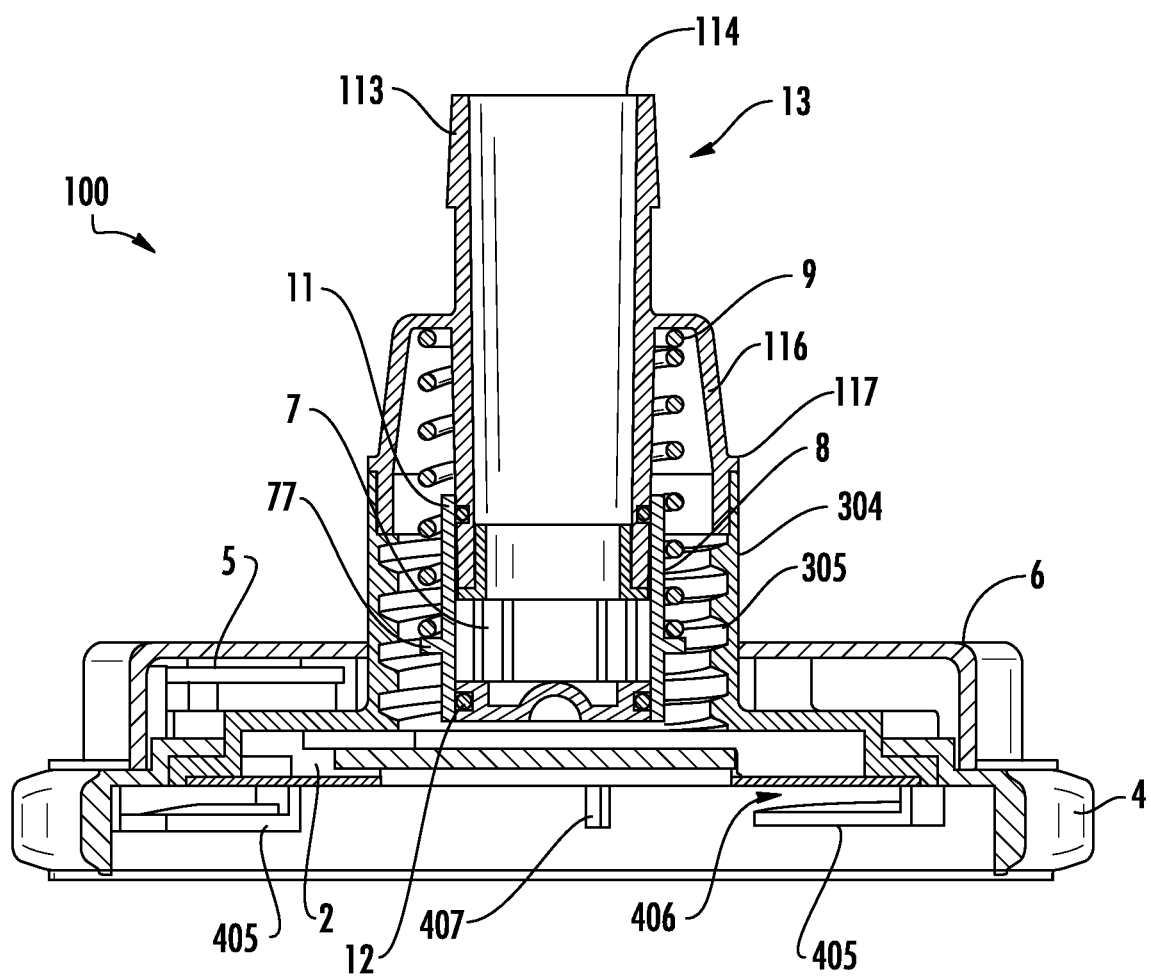
FIG. 3 is a cross-sectional view of the first member taken along line A-A of FIG. 2.
Figure 4:
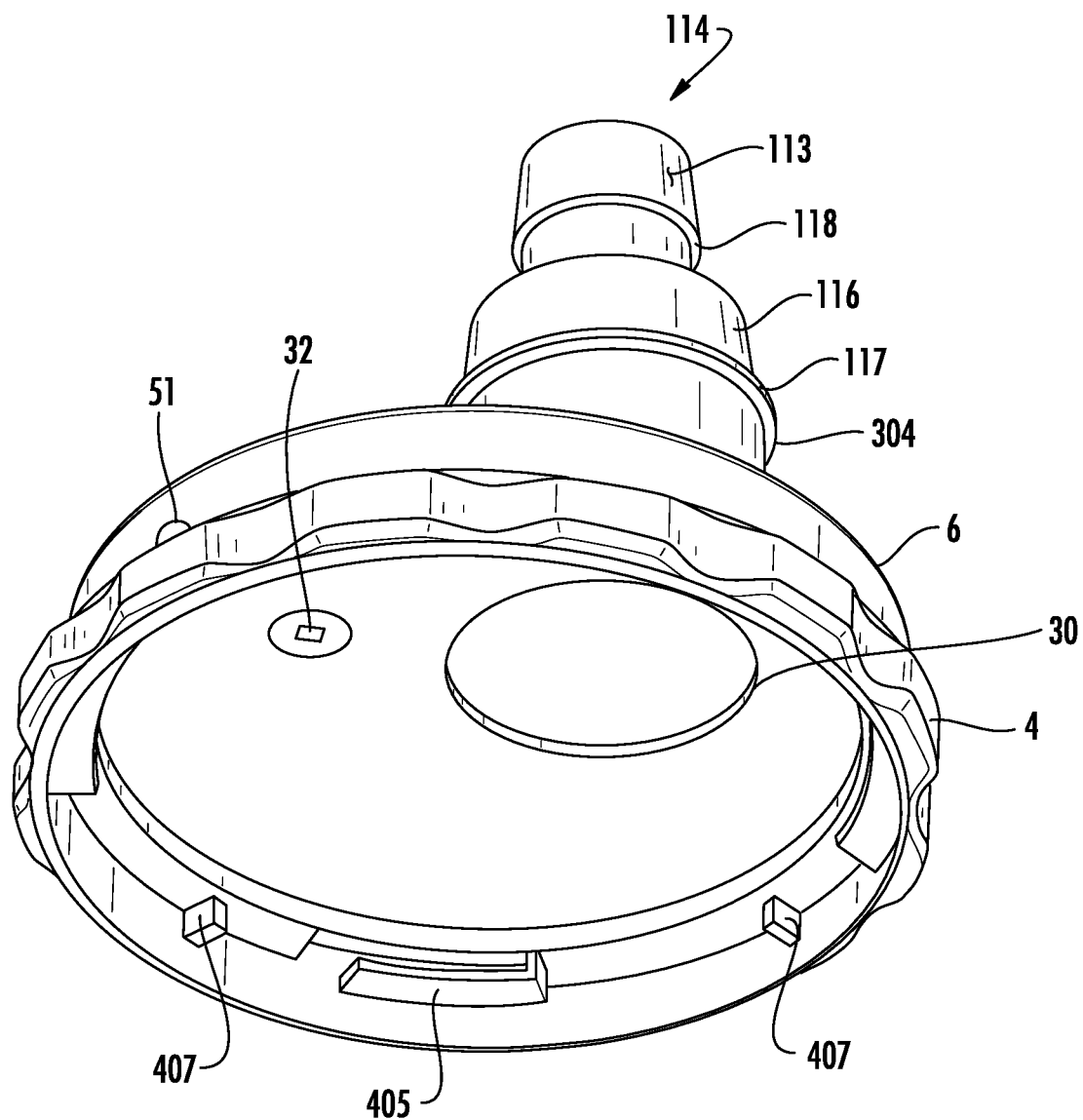
FIG. 4 is a perspective bottom view of the first member of the device of FIG. 1.

The first member or housing 100 also includes a first body member 3, which includes an aperture 33 that receives an axially extending shaft member 32' of door 2, and is sealed with O-ring 10. Thus, the door is pivotable about the axis defined by shaft member 32', between the sterility housing plate 1 and the body member 3, to allow or prohibit fluid communication from the port 30 in plate 1, through port 303, to the cylindrical member 304 of first body member 3. In accordance with certain embodiments, the first body member 3 has a base 300, an axially extending annular shoulder 41, and an outer annular rim 302 formed radially outwardly from the shoulder 41 and extending axially. The member 3 also includes a port 303 that leads to cylindrical member 304 extending axially from the base 300 in a direction opposite that of axially extending rim 302. The cylindrical member 304 includes an internal groove or grooves 305 formed in the inner cylindrical wall of the cylindrical member 304. As best seen in FIG. 3, the groove or grooves 305 terminate prior to the free end of the cylindrical member 304. A door lever 5 sits on top of base 300 of the body member 3. The door lever 5 has an axially extending end portion 5' that sits in a slot defined by two spaced axially extending protrusions 80, 81 on the base 300 (FIG. 2). In certain embodiments, the door lever 5 is attached to the door by an opening in the lever sliding over a feature on shaft member 32'.

The first member or housing 100 also includes first bayonet ring 4, which preferably has a knurled circumferential outer surface as shown, to facilitate the user grasping the ring and rotating it. The bayonet ring 4 has an inner annular shoulder 420 and a keyed locking mechanism coupled thereto for attaching to the second member 200 as discussed in greater detail below. In accordance with certain embodiments, the locking mechanism includes a plurality of slots 406 spaced along the perimeter of the shoulder 420, each slot defined by an L-shaped member 409 that extends axially from the shoulder 420. Positioned between the spaced slots is a plurality of spaced stopping members 407.

The first member or housing 100 also includes a cover 6 having a base 610 and an annular axially extending rim 612. The cover 6 has an aperture 615, preferably circular, that aligns with and receives cylindrical member 304 when in the assembled condition.

The first member or housing 100 includes inner body member 7 that is surrounded by valve shutoff sleeve 8, is positioned in the cylindrical member 304 and sits over wiper seal 12. The sleeve 8 is generally cylindrical, and includes an outer circumferential radially extending flange 77 that serves as a seat for biasing member or spring 9, which fits over the outer cylindrical wall of the sleeve 8.

The first member or housing 100 also includes first base member 13, which includes an axially extending generally cylindrical member 113 terminating in a free distal end having distal opening or outlet 114, and extending axially to a free proximal end having a proximal end 115. The distal region of the member 13 tapers radially outwardly towards the proximal end, thereby forming a shoulder 118. This creates a region of increase radial thickness that helps act as a barb-like fitting and facilitates connection to a tube or the like. The base member 13 includes a generally frusto-conical region 116 that surrounds cylindrical member 113, the region 116 having a circumferential radially extending flange 117 that sits on the rim of the cylindrical member 304 when in the assembled condition (FIG. 3). An annular groove 119 in the proximal region of the member 113 receives O-ring 11 to seal against the sleeve 8, as best seen in FIG. 3.

Figure 5:
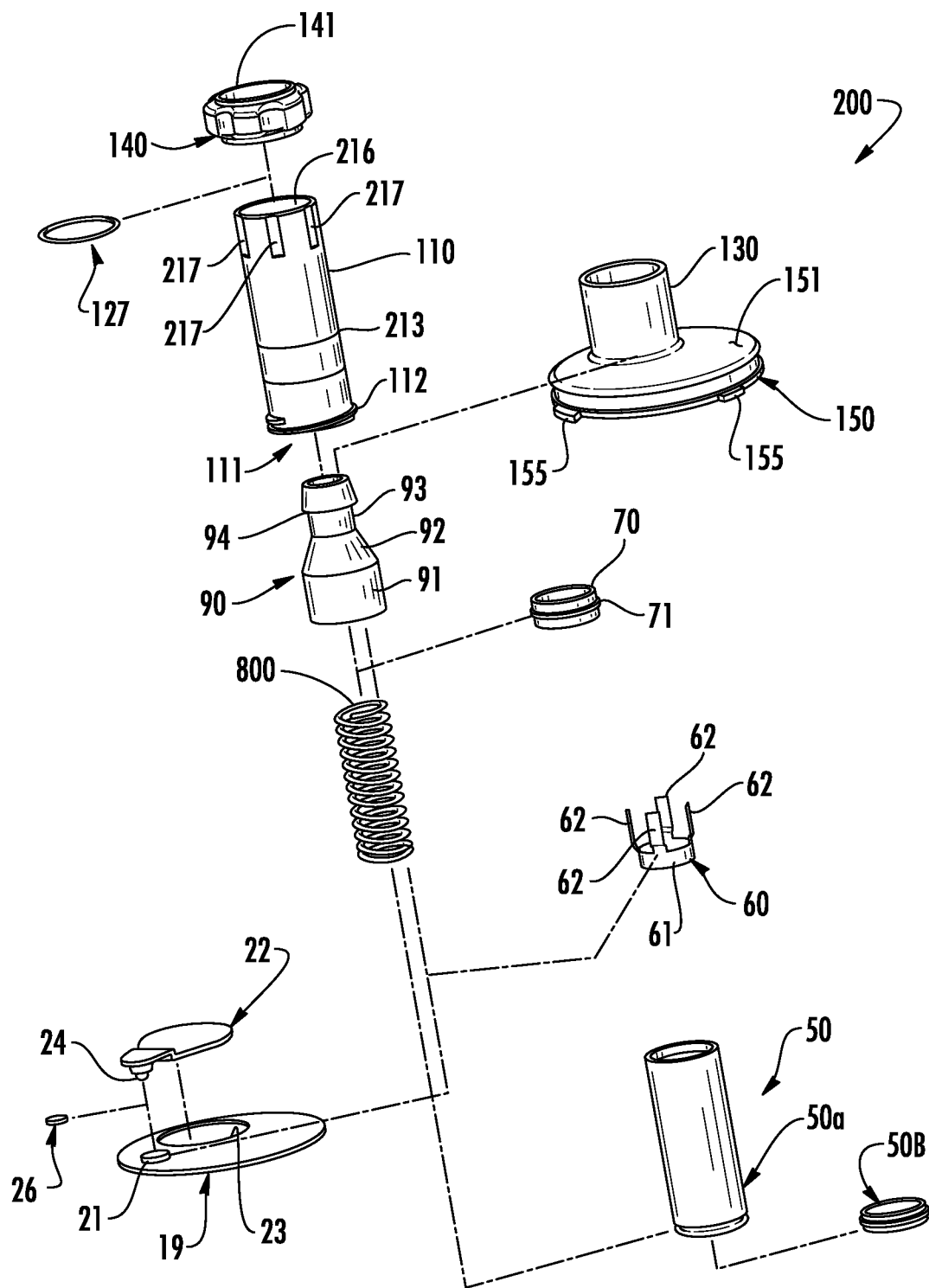
FIG. 5 is a perspective exploded view of a second member of the device in accordance with certain embodiments.
Figure 6:
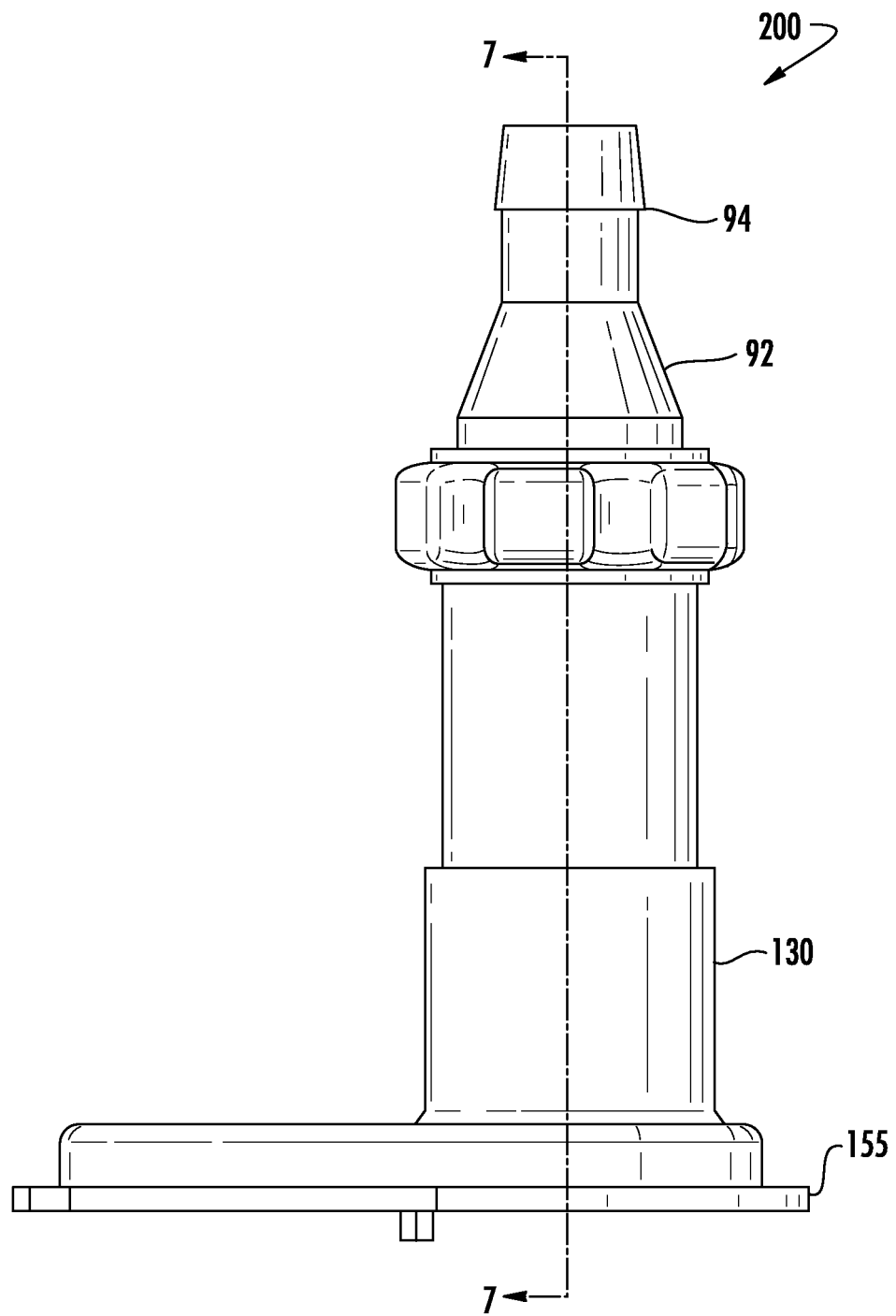
FIG. 6 is a side view of a second member of the device in an assembled condition in accordance with certain embodiments.
Figure 7:
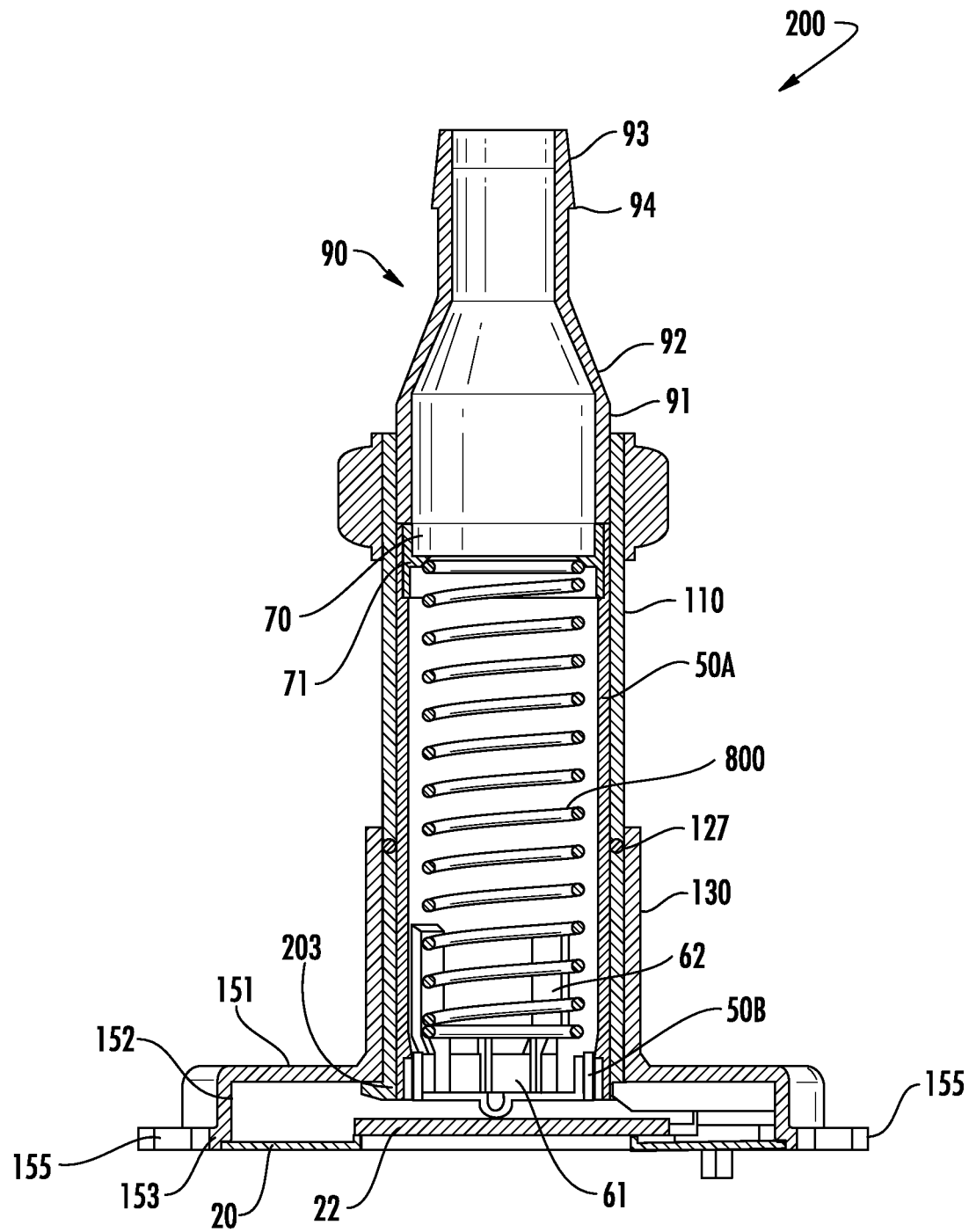
FIG. 7 is a cross-sectional view of the second member taken along line A-A of FIG. 6.

Turning now to FIGS. 5-7, there is shown a second member or housing 200 of the fluid sampling device in accordance with certain embodiments. The second member 200 includes a second sterility housing plate 19 having a port 23, which is preferably circular, that may be closed or blocked by movable second door 22. Door 22 includes an axially extending shaft member 24 that fits into aperture 21 on second sterility housing plate 19 and about which the door 22 is pivotable to block or unblock the port 23. The door 22 is sealed in aperture 21 by door shaft seal 26.

The second member or housing 200 also includes a poppet 60, which includes a base portion 61 and a plurality of spaced legs 62 extending axially from the base portion 61. Those skilled in the art will appreciate that although four legs 62 are shown, the number of legs is not particularly limited. The legs 62 retain a biasing member or spring 800 that is positioned internally of the legs 62, as best seen in FIG. 7.

Figure 8:
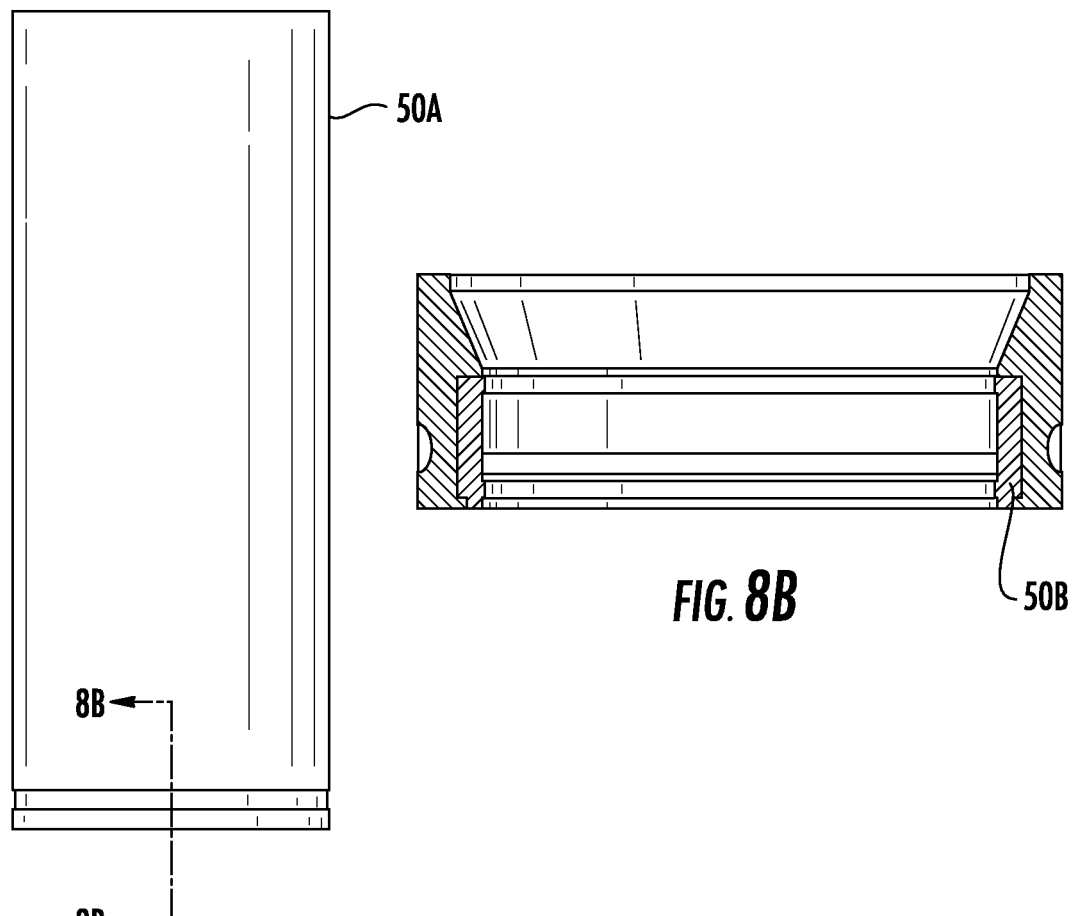
FIG. 8A is a front view of an overmolded inner sleeve in accordance with certain embodiments.
FIG. 8B is a cross-sectional view taken along lines B-B of FIG. 8A in accordance with certain embodiments.

Overmolded inner sleeve 50 includes tubular member 50A that is positioned around spring 800 and poppet 60, and over-mold seal 50B that seats in an annular groove at the base of the tubular member 50A, as shown in detail in FIGS. 8A and 8B. A connector body 70 has an annular radially extending flange 71 having a diameter greater than the inner diameter of the tubular member 50A, allowing the flange 71 to sit on the free end rim of the tubular member 50A a shown in FIG. 7. The portion of connector body 70 below the flange 71 has an outer diameter less than an inner diameter of the tubular member 50A, allowing that portion to sit inside the tubular member 50A. Similarly, the portion of connector body 70 above the flange 71 has an outer diameter less than the inner diameter of the lower free end of inner body 90, which is reduced in thickness relative to the remainder of inner body 90, allowing that portion to sit inside the inner body 90. The inner body includes a lower cylindrical region 91, an intermediate frusto-conical region 92, and an upper cylindrical region 93. The upper cylindrical region 93 includes a portion that extends radially outwardly towards the intermediate frusto-conical region 92, thereby forming a shoulder 94. This region of increase radial thickness helps acts as a barb-like fitting and facilitates connection to a tube or the like.

The second member 200 also includes a generally cylindrical second member valve sleeve 110, which includes a proximal free end 111 formed with an external thread or threads 112 configured to engage the groove or grooves 305 in the first member 100. A circumferential groove 213 is provided to receive O-ring 127 that seals against cylindrical member 130 of the second body 150 as discussed below. Distal free end 216 of the sleeve 110 includes a plurality of spaced slots 217 that receive corresponding spaced projections 141 on nut 140. As best seen in FIG. 7, the valve sleeve 110 is positioned over the inner sleeve 50, the connector body 70, and a portion of the lower cylindrical region 91 of the inner body 90.

The second member 200 includes a second body 150 having a base 151, an axially extending annular shoulder 152, and an outer annular rim 153 formed radially outwardly from the shoulder 152 and extending axially. The member 200 includes a port 203 that leads to cylindrical member 130 extending axially from the base 151 in a direction opposite that of axially extending shoulder 152. The door 22 is pivotable about the axis defined by shaft member 24, between the sterility housing plate 19 and the second body 150, to allow or prohibit fluid communication from the port 23 in plate 19, through port 203, to the cylindrical member 130 of the second body 150. Extending radially outwardly from the rim 153 is a plurality of spaced tabs 155 configured to be received in the slots 406 in the bayonet ring 4 of the first member 100.

In operation, the second member 200 and first member 100 are brought together such that the sterility housing plates 1 and 19 are in opposing relation. Relative rotation of the first and second members is created, such as by rotating the bayonet ring 4, causing the tabs 155 in the second member to enter the slots 460 of the first member and lock the members together. This relative rotation also causes the alignment of the ports 30 and 23 in the sterility housing plates 1 and 19, which are opposed. Fluid communication between the first and second members is created, as the relative rotation also causes the doors 2 and 22, which were previously blocking the ports in the respective sterility housing plates and the ports in the respective body members, to pivot to an open position. Once the doors are in the open position, the second member valve sleeve 110 is axially displaced through the port 23 in sterility housing plate 19, and through the port 30 in sterility housing plate 1. The second member valve sleeve 110 is then rotated with nut 140, and is further displaced axially, causing the thread or threads 112 to engage and mate with the groove or grooves 305 in cylindrical member 304 of base 300. This causes the axial displacement of valve shutoff sleeve 8, compressing spring 9. A sterile connection is thus made, and fluid can be transferred.

Once fluid transfer is complete, the second member or housing 200 is retracted from the first member or housing 100. Thus, the nut 140 is rotated, causing the threads 112 in the second member valve sleeve 110 to disengage with the grooves 305 in the cylindrical member 304 of base 300. Spring 9 is no longer compressed, and the valve shutoff sleeve 8 is retracted axially to its original position. Wiper seal 12 pushes against base portion 61 and seals and wipes across over-mold seal 50B in tubular member 50A. The seal wipes any liquid that may be present when device is being pulled apart. The second member valve sleeve 110 is then removed from the first member, and the bayonet ring 4 is rotated to cause the doors to block the respective ports, thereby maintaining a sterile environment in each member. The process can then be repeated.

Due to its simplicity, the device can be obtained by simple molding of all the members that constitute it, thus being possible for the device to be a single-use (disposable) device for reasonable cost. The device may also be made from conventional machining of its components from the various plastic and metal materials previously listed.

Figure 9:
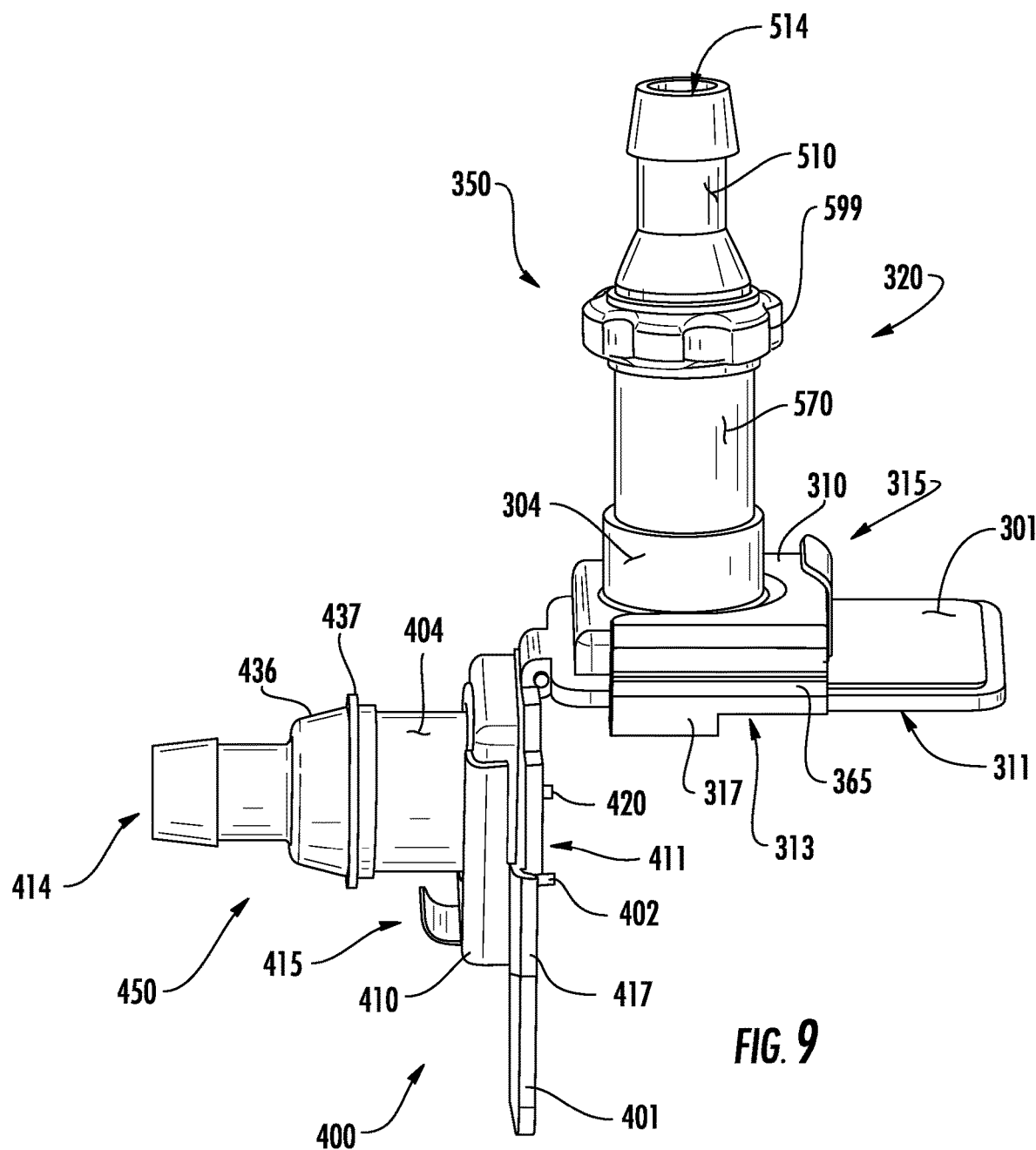
FIG. 9 is a perspective view of a first alternative embodiment of a fluid transfer device.

FIG. 9 illustrates a first alternative embodiment of the fluid transfer device in accordance with certain embodiments. The valve operation of this first alternative embodiment is similar to the earlier embodiment; upon connection of the first and second members, sterile fluid communication is established under pressure by causing displacement of one valve member into another. The primary difference is in the configuration of the body members or housings and the way the members are brought into engagement or are coupled together. For example, the embodiment of FIG. 9 uses a hinged assembly to mate the first and second members or housings.

More specifically, FIG. 9 shows first member or housing 400 and second member or housing 320 in a partially assembled condition. First member or housing 400 includes body member 401 that has pins 402 on opposite sides of the bottom surface of body member 401 for engagement with a corresponding slot 313 in the body member 301 of second member 320. Similarly, second member 320 includes body member 301 that has pins 312 on opposite sides of the bottom surface of body member 301 for engagement with a corresponding slot 403 in the body member 401 of first member 400. Body 301 of second member 320 includes a slidable locking handle assembly 310. Body 401 of first member 400 includes a slidable locking handle assembly 410.

Figure 11A:
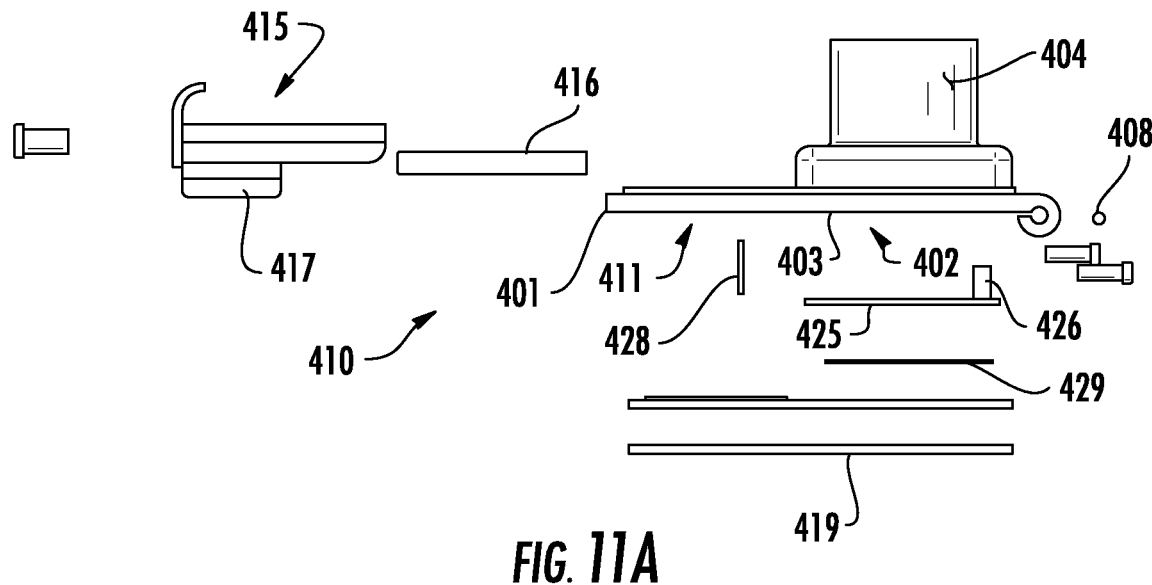
FIG. 11A is an exploded view of a portion of the first alternative embodiment of a fluid transfer device.

Slidable locking handle assembly 410 is shown in greater detail in FIG. 11A. It includes handle member 415, spaced door shafts 416 (only one shown), door 425 and door stop 426. The door shafts 416 are coupled to the handle member 415 and slide in respective apertures 323 in the body member 401 (FIG. 12). The handle assembly 410 includes spaced radially projecting L-shaped flanges 417 (only one shown in FIG. 11A) that slide on respective opposite edges of the body member 401. When in the closed position, the flanges 417 of handle assembly 410 fit in corresponding reduced in thickness regions in the body member 301, which enables the first and second members to mate. Sliding the handle assembly 410 to the locked position moves the flanges 417 away from the reduced in thickness regions in the body member 301 and cooperatively with handle assembly 310, clamps the first and second members together.

In certain embodiments, door 425 is a generally flat member configured to block the port in the second member 320, preventing fluid communication between the first and second members 400, 320. In certain embodiments, the door 425 seals against overmolded gasket 429 that is positioned on the inside of the bottom sterile face 411 of the body member 401. An overmolded sterile plate gasket 419 is a perimeter gasket that can be overmolded onto the housing beyond the edge of the sterile plate 411 to seal against the corresponding second member sterile plate when the first and second members are brought together, to keep out contaminants.

Projecting upwardly from the door 425 is a door stop 426, which when the door 425 is in the fully open position, abuts against a wall in the body member 401 to delimit the door open position.

In certain embodiments, wiper seal 428 is positioned in the body member 401 so that as the door 425 is actuated from its closed to its open position, and vice versa, it contacts the wiper seal 428. The wiper seal 428 isolates the door in the open position from the region of the device where fluid flows. This helps to maintain sterile the area where fluid flows.

Figure 11B:
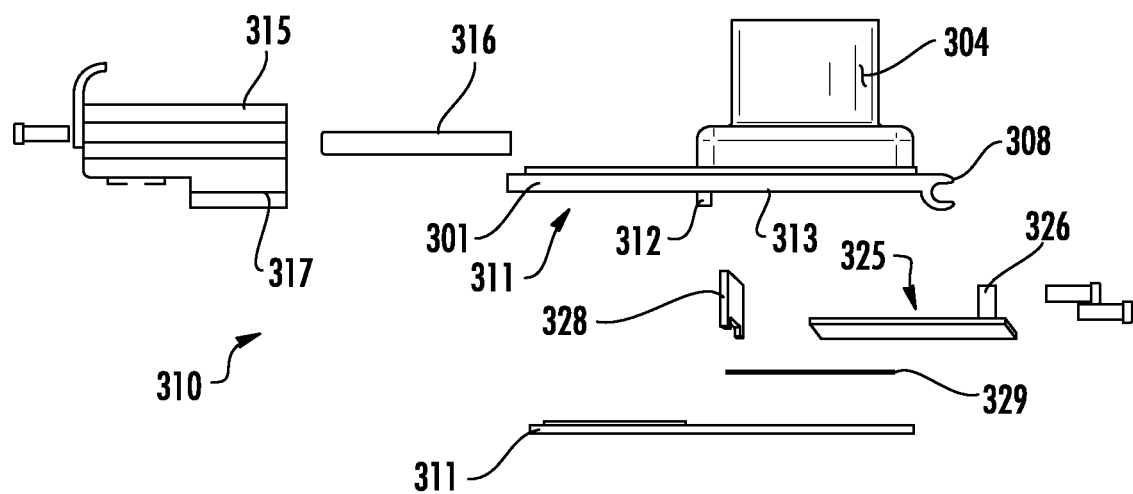
FIG. 11B is an exploded view of another portion of the first alternative embodiment of a fluid transfer device.

The handle assembly 310 of second member 320 has a similar construction, as shown in FIG. 11B. It includes handle member 315, spaced door shafts 316 (only one shown), door 325 and door stop 326. The door shafts 316 are coupled to the handle member 315 and slide in respective apertures (not shown) in the body member 401. The handle assembly 310 includes spaced radially projecting L-shaped flanges 317 (only one shown in FIG. 11B) that slide on respective opposite edges of the body member 301. Sliding the handle assembly 310 to the locked position cooperatively with handle assembly 410 clamps the first and second members together.

In certain embodiments, door 325 is a generally flat member configured to close the port in the second member 320, preventing fluid communication between the first and second members 400, 320. In certain embodiments, the door 325 seals against overmolded gasket 329 that is positioned on the inside of the bottom sterile face 311 of the body member 301. Projecting upwardly from the door 325 is door stop 326, which when the door 325 is in the fully open position, abuts against a wall in the body member 301 to delimit the door open position.

In certain embodiments, wiper seal 328 is positioned in the body member 301 so that as the door 325 is actuated from its closed to its open position, and vice versa, it contacts the wiper seal 328. The wiper seal 328 isolates the door in the open position from the region of the device where fluid flows. This helps to maintain sterile the area where fluid flows.

Figure 25:
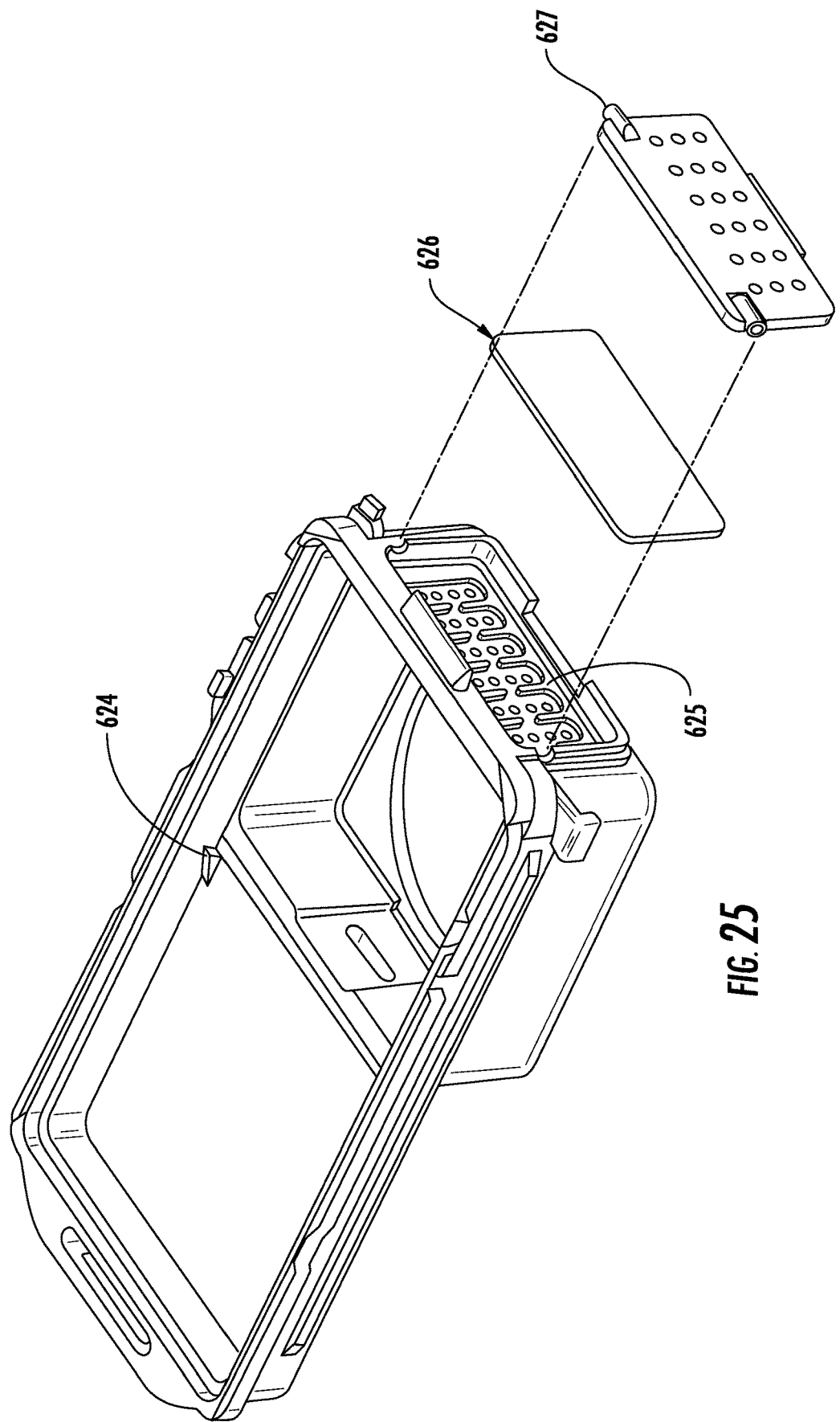
FIG. 25 is a perspective view of a vent and vent membrane incorporated into a housing in accordance with certain embodiments

In certain embodiments, a vent 625, vent membrane 626 and vent cover 627 may be incorporated into the housing, to draw in ambient air as the valve member is retracted (FIG. 25). A suitable membrane 626 is a 0.22 micron sterilizing membrane. The vent 626 may include a plurality of holes communicating with the housing interior, which provide a path for air to enter the device when the valve is retracted from the female housing which creates a syringe effect. Air that is pulled in flows through the vent 626 and is sterilized by the membrane 626. In certain embodiments, the vent membrane 626 can be heat sealed to the housing, but gaskets could be used or a pre-existing filter could be attached to a port in the housing.

Figure 10A:
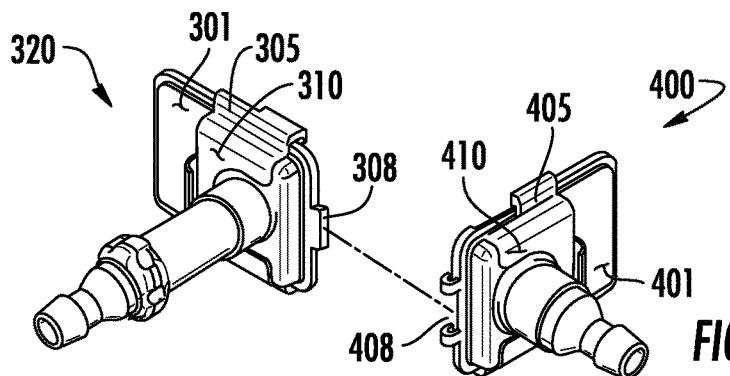
FIG. 10A is a perspective view of the first alternative embodiment of a fluid transfer device in a pre-engaged or coupled position.
Figure 10B:
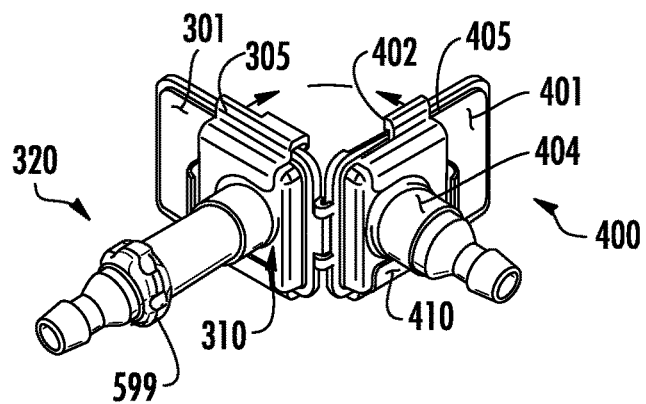
FIG. 10B is a perspective view of the first alternative embodiment of a fluid transfer device in a partially engaged or coupled condition.
Figure 10C:
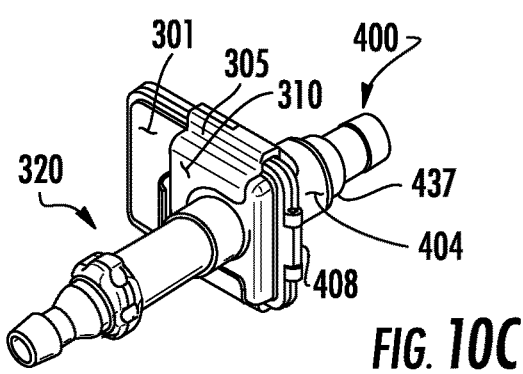
FIG. 10C is a perspective view of the first alternative embodiment of a fluid transfer device in an engaged or coupled position.
Figure 10D:
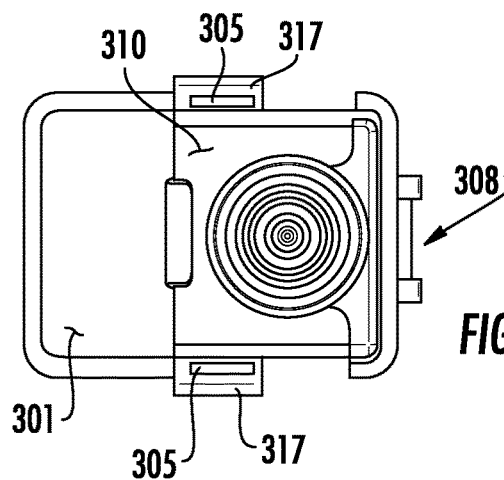
FIG. 10D is a top view of a portion of the first alternative embodiment of a fluid transfer device.

To assemble the transfer device, the first member 400 and second member 320 are oriented at 90° as shown in FIG. 10A, the members are brought into engagement such that the hinge pin 408 on body member 401 can be inserted into the slot 308 on body member 301 as shown in FIG. 10B, the body members 301, 401 thereby forming a clamshell-like configuration. The clamshell is closed by bringing the ends opposite the hinge of members 320 and 400 together, rotating about the axis of the hinge pin 408 as shown by the arrows in FIG. 10B. The closed, assembled position is shown in FIG. 10C. In this position, the locking handle assemblies 310, 410 mate so that sliding actuation of one handle also actuates the other. In this position, the valve is closed by doors 425, 325; there is no fluid communication between the first member 400 and the second member 320.

Upon connection of first and second members or housings 400, 320, each of the pins 312 enters a respective slot 403 in the first member 400, and displaces locking member 405 axially, moving it out of the path of slidable handle assembly 410. Similarly, each of the pins 402 enters a respective slot 313 in the second body member 320, and displaces locking member 365 axially, moving it out of the path of slidable handle assembly 310. In certain embodiments, each locking member 365, 405 is an elongated member having a free end that is axially displaceable.

Once the first and second members or housings 400, 320 are in engaging relation, the locking handle assemblies 310, 410 are actuated by sliding them to the left as depicted in FIG. 10C. This actuation simultaneously locks the members 320, 400 together, and moves the doors in each member to the open position, which establishes fluid communication between the first and second members 400, 320. Once fluid communication is established, the valve member of the second member 320 can be displaced into the valve member of the first member 400, as discussed in greater detail below.

FIGS. 13A-13C illustrate the first member valve member 450. Fitting 413 includes an axially extending generally cylindrical member terminating in a free distal end having distal opening or outlet 414, and extending axially to a free proximal end 435 that sits over the upper free end of cylindrical member 404 of first member 400 (FIG. 12). The distal region of the fitting 413 tapers radially outwardly towards the proximal end, thereby forming a shoulder 418. This creates a region of increase radial thickness that helps act as a barb-like fitting and facilitates connection to a tube or the like. The fitting 413 includes a generally frusto-conical region 436, the region 436 having a circumferential radially extending flange 437 that sits on the rim of the cylindrical member 404 of first member 400 when in the assembled condition of FIG. 10C.

Wiper seal 442 is a generally cylindrical member, and includes an intermediate outer circumferential radially extending flange 477 that serves as a seat for biasing member or spring 479 which fits over the downwardly projecting member 439 in fitting 413.

Base member 480 has an upper cylindrical portion that seals inside wiper seal 442 with the aid of O-ring 486. The lower region 484 of the base member 480 includes a downwardly facing depressor member 481 that in the embodiment shown extends axially from the member 480 and has a semispherical shape. It functions to displace the poppet 560 in the corresponding valve member 350 of the second member 320 upon actuation of the valve, as discussed in greater detail below.

FIGS. 14A-14E show the valve member 350 of the second member or housing 320. The valve member 350 includes upper inner body 510. Upper inner body 510 includes an axially extending generally cylindrical member terminating in a free distal end having distal opening or outlet 514, and extending axially to a free proximal end having a proximal end opening 535. The distal region of the inner body 510 tapers radially outwardly towards the proximal end, thereby forming a shoulder 518. This creates a region of increase radial thickness that helps act as a barb-like fitting and facilitates connection to a tube or the like.

The valve member 350 also includes a poppet 560, which includes a solid base portion 561 and a plurality of spaced legs 562 extending axially from the base portion 561. Those skilled in the art will appreciate that the number of legs is not particularly limited. The base portion 561 includes a centrally located detent 559 that receives projection 482 on the depressor member 481, as discussed in greater detail below. The legs 562 retain a biasing member 580 such as a compression spring or the like that is positioned internally of the legs 562. The opposite end of the biasing member 580 sits in inner body connector 594, which is shown in greater detail in FIG. 14D. Inner body connector 594 includes an intermediate annular ring 593 that seats between the gap between lower edge of upper inner body 510 and the upper edge of valve lower inner body 575. The ring 593 extends radially inwardly to provide a seat for biasing member 580.

Valve outer sleeve 570 is a generally cylindrical member that has threads 571 at its lower end for engaging corresponding grooves 318 (FIG. 12) in the generally cylindrical member 404 of first member 400. The lower portion of upper inner body 510 sits inside the valve outer sleeve 570 as seen in FIG. 14C, as does inner body connector 594, biasing member 580, poppet 560, and lower inner body 578. The lower inner body 578 is generally cylindrical, and as shown in FIG. 14E, includes at its lower end radially inwardly extending flanges 577, which hold an overmolded seal 579 to seals against poppet 560.

In certain embodiments, relative linear displacement of the valve members 350, 450 into each other is effectuated by applying an axial load. In certain embodiments, the valve member 350 of the second member 320 is linearly displaced into the valve member 450 of the first member 400, and then further displacement of the valve member 350 into the valve member 450 is effectuated by relative rotation of the valve members, such as by rotating the valve member 350 of the second member 320 with knob 599. This rotation causes the thread or threads 571 on the valve outer sleeve 570 to engage the corresponding groove or grooves 318 in the cylindrical member 404 of valve member 450. Continued relative rotation further displaces the valve member 350 into valve member 450, causing the depressor member 481 to contact and displace poppet 560 in a first direction against the bias of biasing member 580. Still further rotation causes the threaded end of valve member 350 to engage the radial flange 477 of wiper seal 442, causing the latter to displace in a second direction against the bias of biasing member 479. In certain embodiments, the first and second directions are opposite directions. The displacements of the poppet 560 and of the wiper seal 442 create fluid communication between and through the valve members 350, 450.

Figure 15:
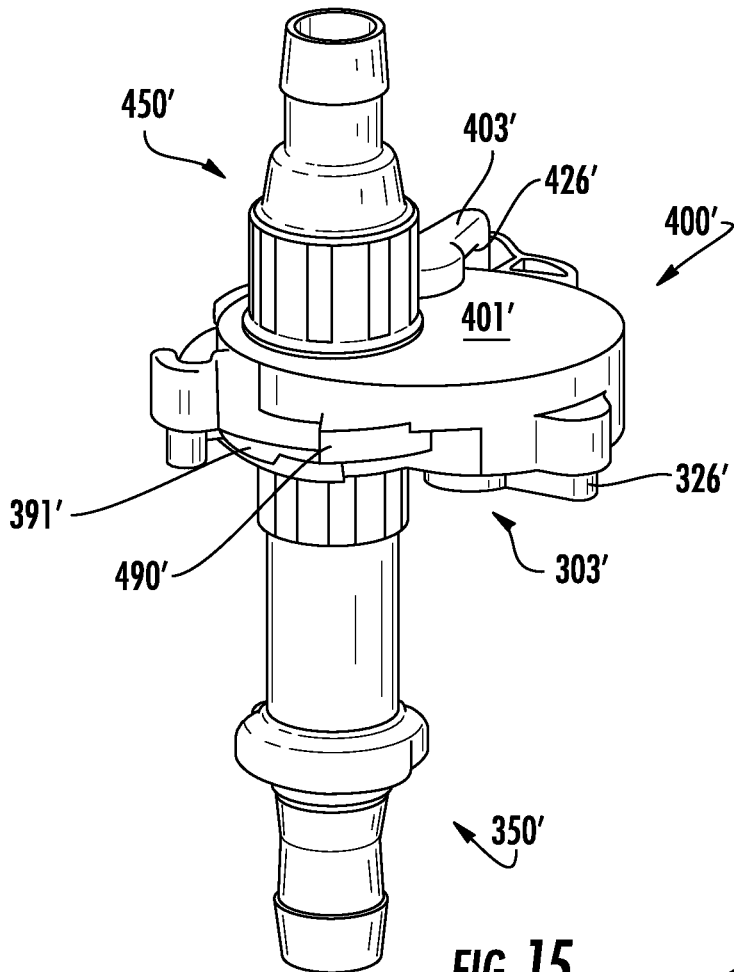
FIG. 15 is a perspective view of another alternative embodiment of a fluid transfer device.
Figure 16:
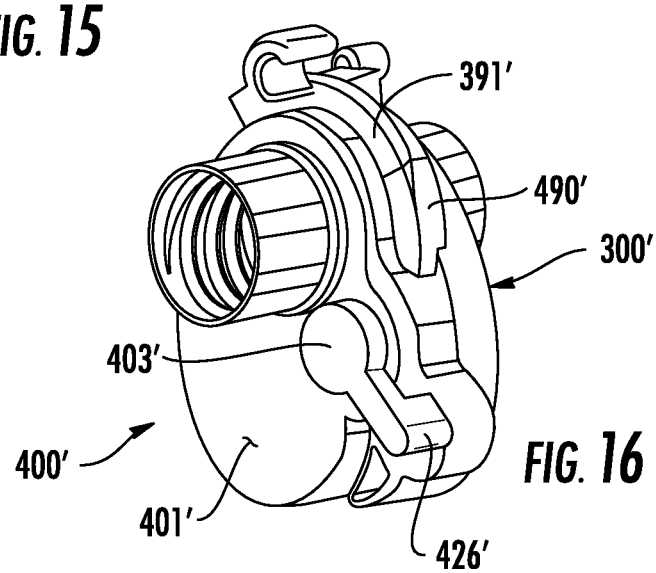
FIG. 16 is a perspective view of a portion of the fluid transfer device of FIG. 15.

FIGS. 15 and 16 illustrate a second alternative embodiment of the fluid transfer device in accordance with certain embodiments. The valve operation of this second alternative embodiment is similar to the first alternative embodiment; upon engagement and locking of the first and second members or housings, sterile fluid communication is established under pressure, and displacement of one valve member into another can be carried out. The primary difference is in the configuration of the body members or housings and the way the members are brought into engagement. For example, the embodiment of FIGS. 15 and 16 involve the alignment of pin and hook features followed by engaging cam locks (FIG. 16) on the faces of the body members or housings.

More specifically, FIGS. 15 and 16 show first member or housing 400' and second member or housing 300' in an assembled condition. The valve members 350', 450' are the same or essentially the same as the valve members 350 and 450 of the first alternative embodiment, and thus will not be discussed in detail here.

The housing for the valve members (shown in FIG. 16 without the valve members in place) includes a first member or housing 400' having body member 401' that has a shaped bottom region that corresponds to a similarly shaped bottom region of second member or housing 300', allowing the first and second members to mate. Each member 400', 300' includes a top plate. In certain embodiments, each member 400', 300' includes a cam slot (only one shown at 490' for first member 400'), that receives a respective cam member (only one shown at 391' for second member 300') on the other member, each cam member being received by the respective cam slot as the two members 400', 300' are engaged and twisted in opposite directions to lock them together. Each member 300', 400' carries a respective lever arm 303', 403' arm attached to a respective door 325', 425'. Each lever arm is rotatable between a door open and a door closed position. Lever arm 403' of first body member 401' has an axially extending hollow leg 426' that mates with a pin (not shown) that extends axially from the second member 301'. Similarly, lever arm 303' of second body member 301' has an axially extending hollow leg 326' that mates with a pin (not shown) in the bottom of first body member 401'.

In certain embodiments, each body member 401', 301' has a bottom plate having a valve port that is normally closed by a respective door 425', 325'. When the members are in the assembled condition, the valve ports are aligned.

Figure 17:
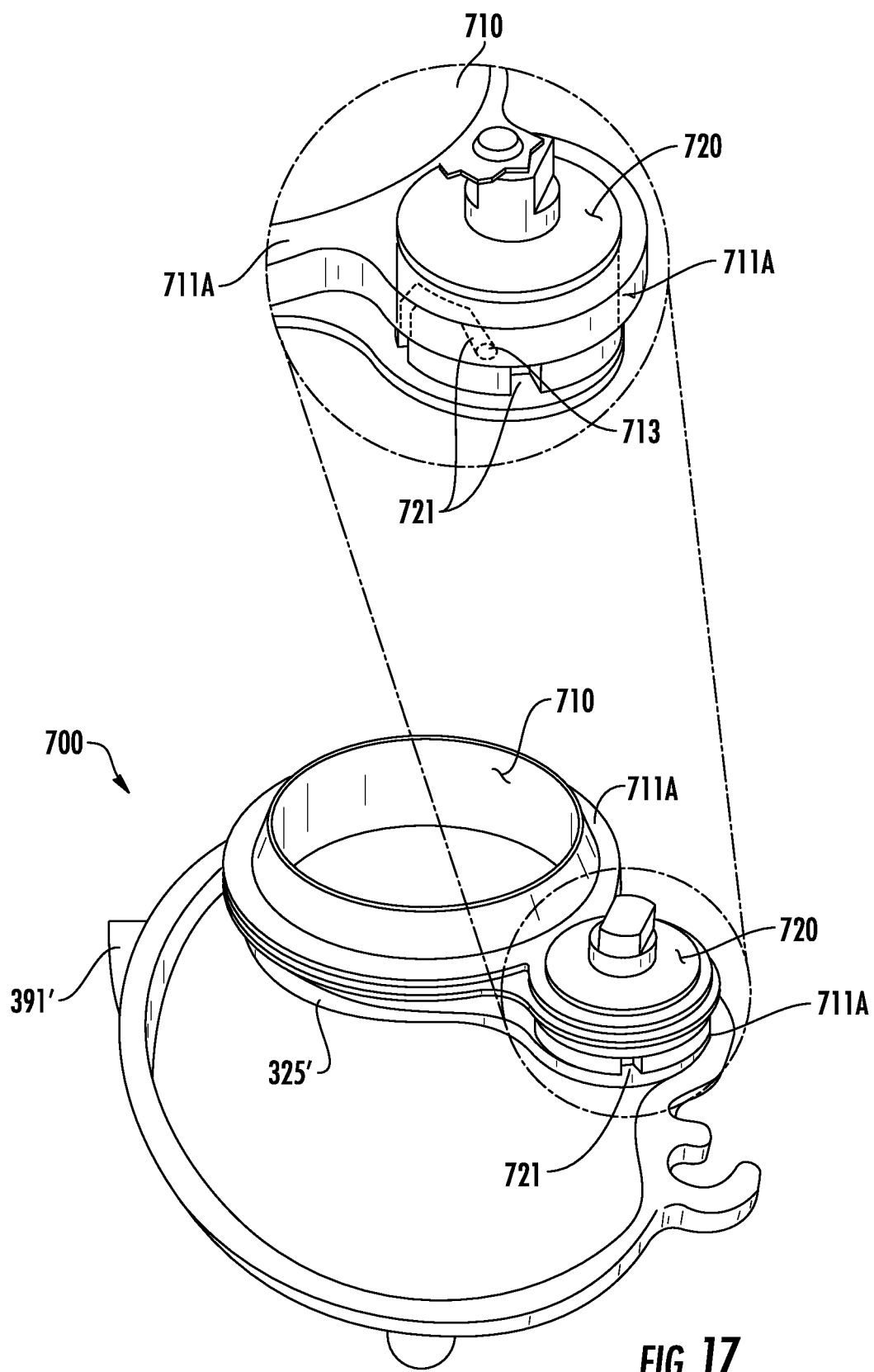
FIG. 17 is a perspective view of a valve isolator bellows assembly in accordance with certain embodiments, showing a portion of the assembly in an exploded view.
Figure 17A:
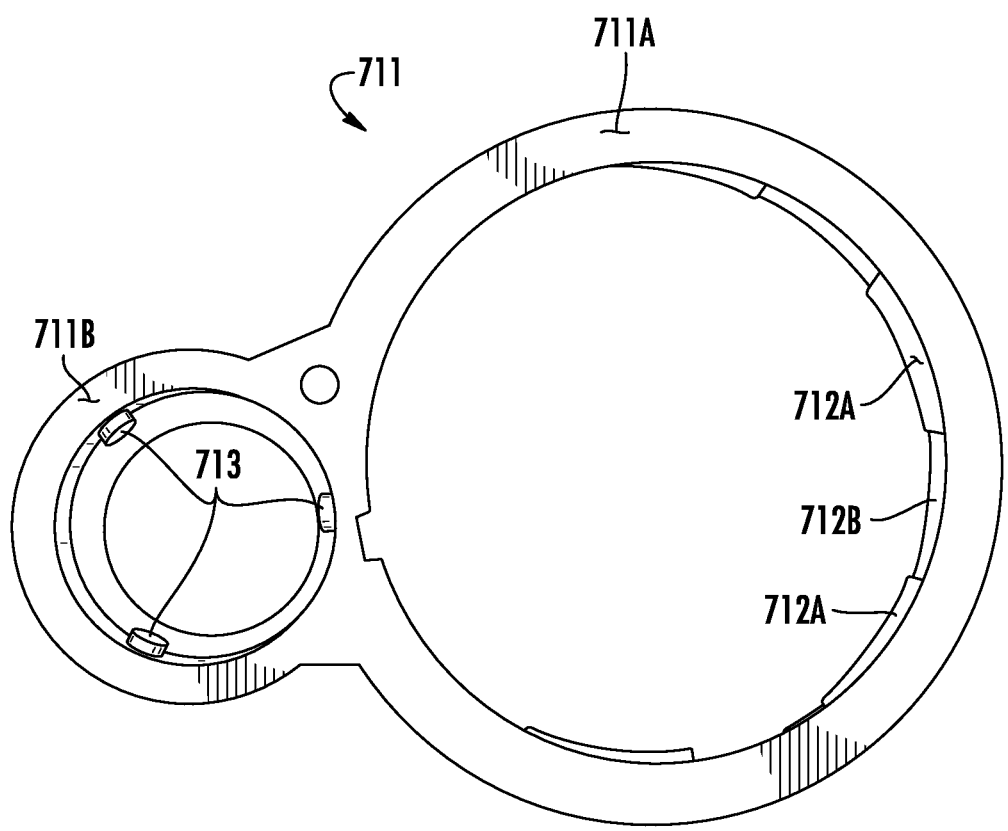
FIG. 17A is a perspective view of a bellows retainer in accordance with certain embodiments.

FIG. 17 illustrates a valve isolator bellows assembly 700. The assembly 700 includes a bellows 710 that is held by seal retainer member 711 (FIG. 17A). Seal retainer member 711 includes a first ring 711A that secures bellows 710, and a second ring 711B that connects to cam member 720. The first ring 711A includes alternating top and bottom radially inwardly extending flanges 712A, 712B that serve to retain the bellows 710. Door 325' also has a ring that connects to cam member 720. Both the door 325' and seal retainer member 711 are moved by rotation of cam 720. In certain embodiments, the cam 720 is generally cylindrical, and includes a plurality of cam slots or grooves 721 (one shown in each of FIGS. 17 and 19A) formed in its outer side surface. There are corresponding spaced pins 713 on the second ring 711B of the seal retainer member 711 that extend radially inwardly, each of which travels in a respective cam slot 721 of the cam 720. In certain embodiments, the second ring 711B includes three such pins 713, and the cam 720 includes three such cam slots 721, each one corresponding to a respective pin.

Figure 17B:
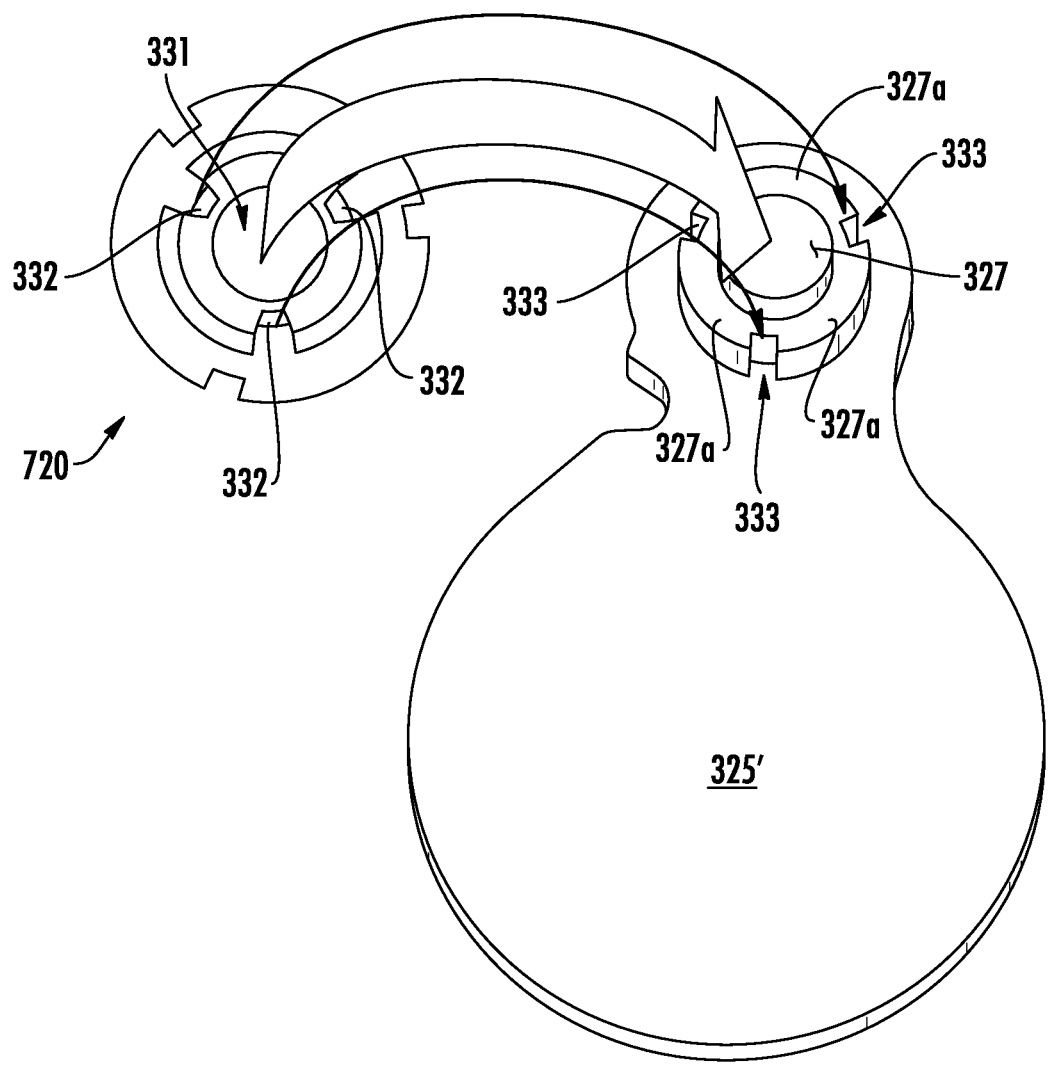
FIG. 17B is a top view of a door and bottom view of a cam in accordance with certain embodiments.
Figure 20:
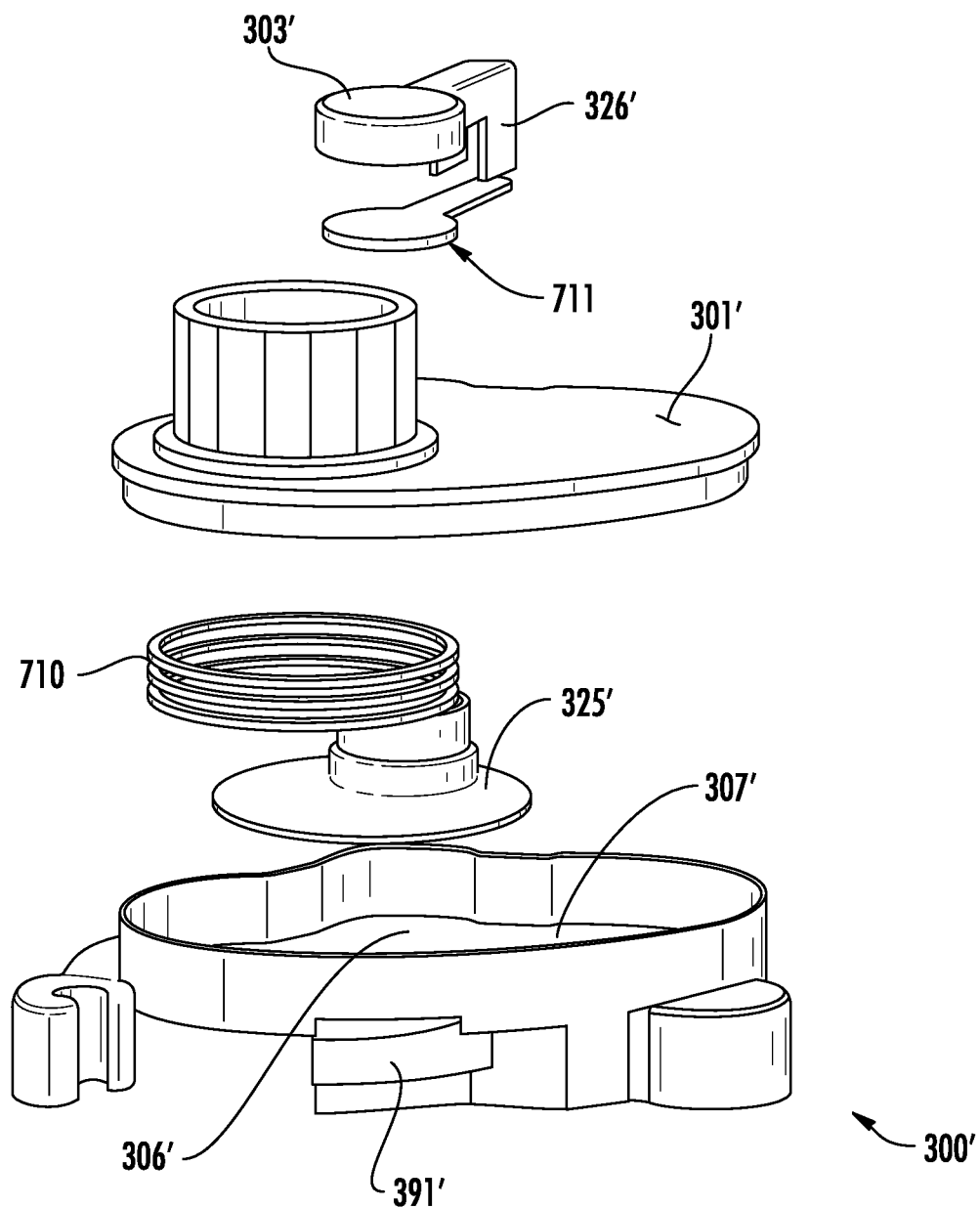
FIG. 20 is an exploded view of the bellows assembly of FIG. 17 and portions of the fluid transfer device housing in accordance with certain embodiments.

In certain embodiments, the door 325' includes a pin (not shown) extending axially downwardly from its bottom to mate with an aperture 306' (FIG. 20) in base 307' of the member 400'. As seen in FIG. 17B, the door includes an axially extending button 327 and a plurality (three shown) of spaced axially extending wings 327A that surround the button 327 but do not extend as high. The button 327 and wings 327A fit into and are engaged by the open region 331 in the underside of the cam 720, the open region 331 including spaced radially inwardly projecting prongs 332 that fit into the spaces 333 between the wings 327A on the door 325' as shown by the solid arrows in FIG. 17B. In certain embodiments, cam 720 includes a keyed pin 723 extending upwardly axially from its top surface to mate with lever arm 303'. Rotation of lever arm 303' causes a corresponding rotation of cam 720. Rotation of the cam moves the door 325' from the open to the closed position (and vice versa), and causes vertical movement of the bellows 710 as the retainer member 711 rides in the cam slots 721 of the cam, as discussed in greater detail below.

Figure 18A:
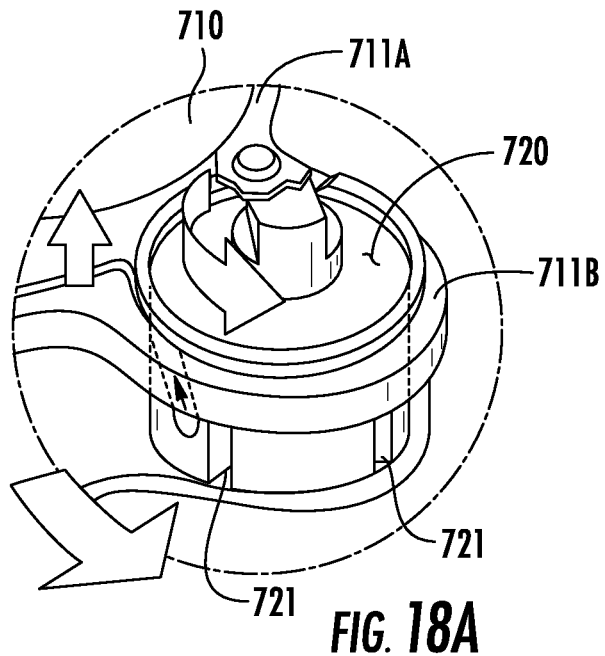
FIG. 18A is a perspective view of a portion of the bellows assembly in accordance with certain embodiments.
Figure 18B:
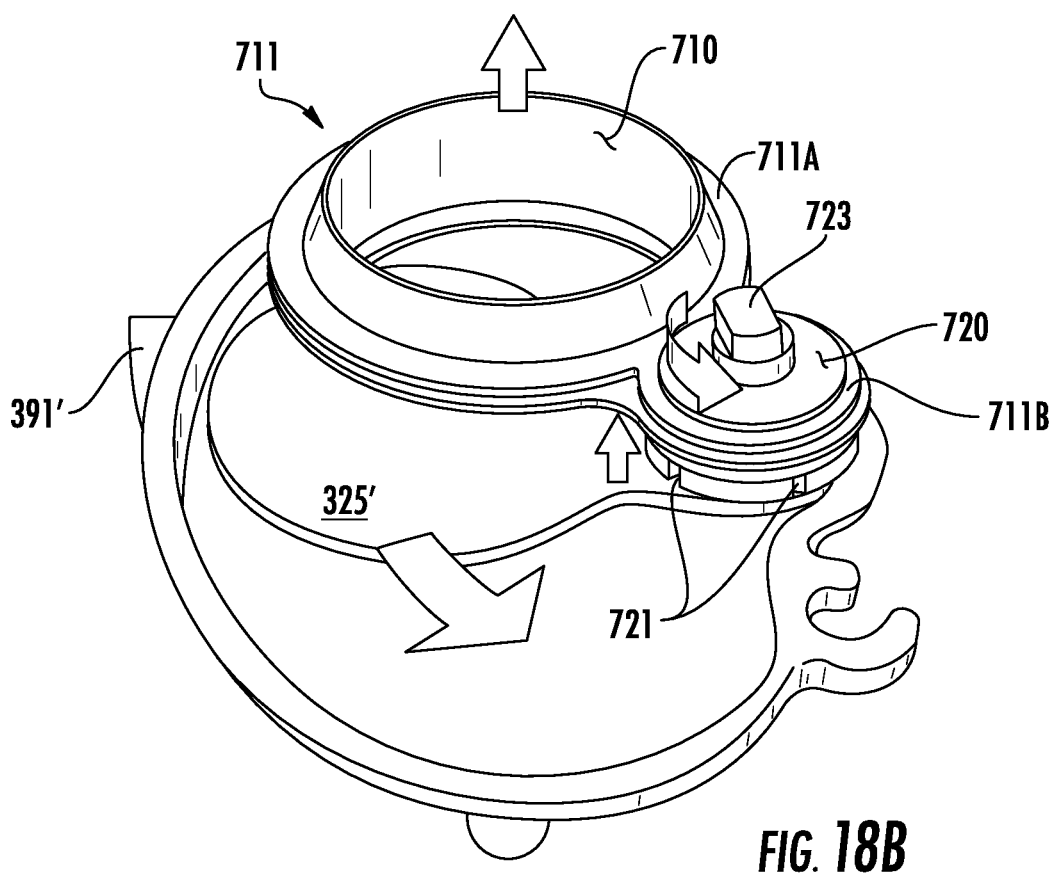
FIG. 18B is a perspective view of the bellows assembly of FIG. 17 showing motion of various elements thereof in accordance with certain embodiments.
Figure 19A:
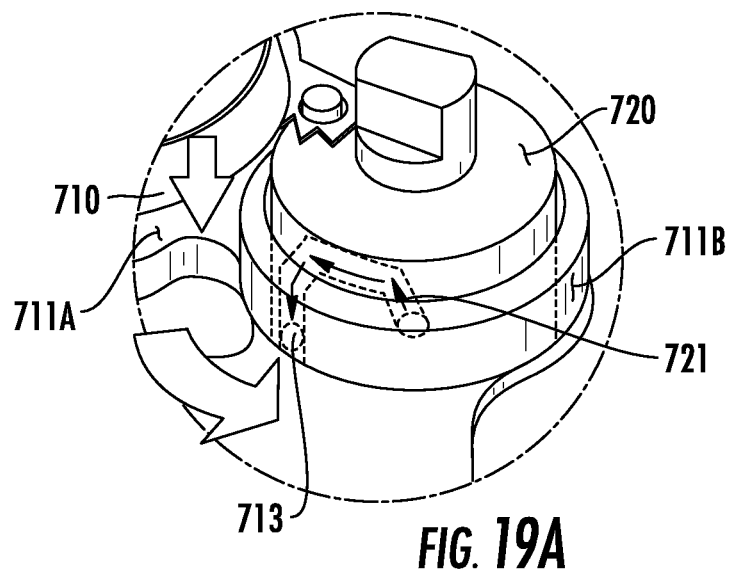
FIG. 19A is a perspective view of a portion of the bellows assembly showing motion of various elements thereof in accordance with certain embodiments.
Figure 19B:
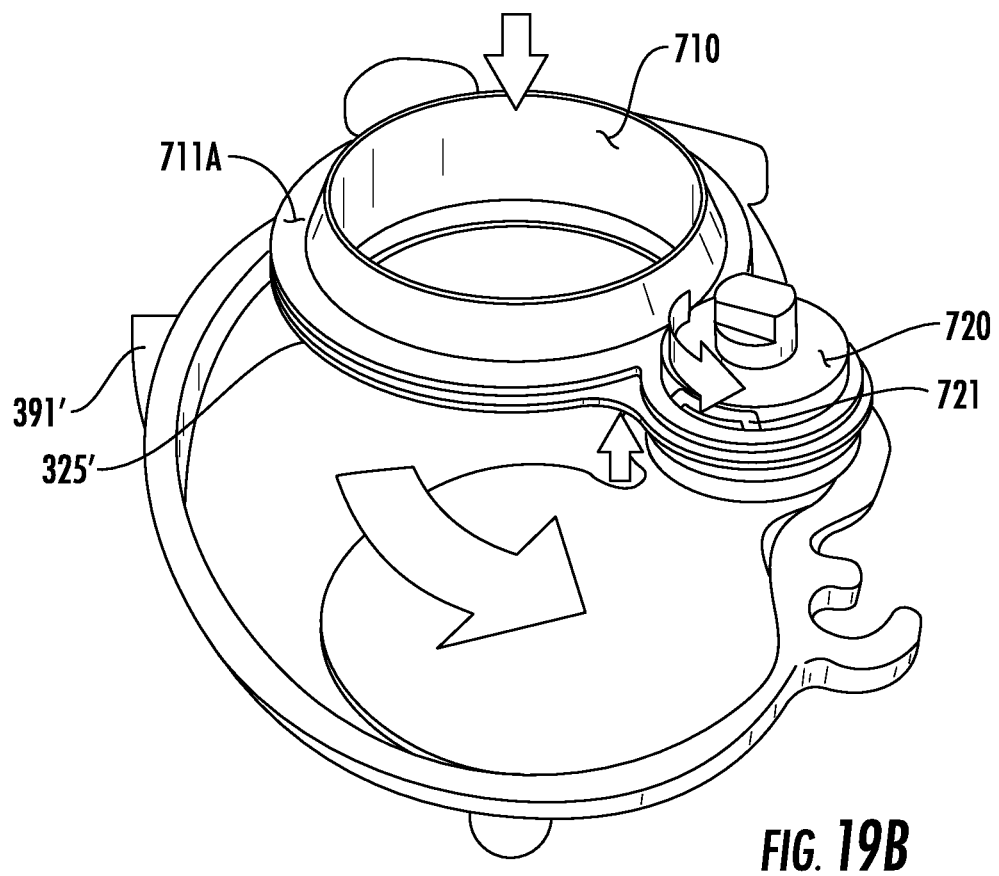
FIG. 19B is a perspective view of the bellows assembly of FIG. 17 showing motion of various elements thereof in accordance with certain embodiments.

FIG. 17 illustrates the door 325' and bellows 710 in the closed position. In this position, the door 325' prevents fluid communication between the valve members, and the bellows 710 is sealed against the door 325'. As lever arm 303' rotates as shown in FIGS. 18A and 18B, the cam 720 coupled to the lever arm also rotates, causing the door to open and the retainer member 711 to ride in the cam slots 721, thereby first moving axially upwardly and then ultimately moving the bellows axially downwardly towards the port in the body member 301' as the bellows seal breaks from the door. Continued rotation of lever arm 303' moves the door to its fully open position, as shown in FIGS. 19A and 19B, and causes bellows to reach its lowest, valve sealing position (as guided by travel in the cam slots 721). In this position, the bellows is over the valve port and seals against the bottom plate 380', protecting the valve members from contamination.

Although the bellows assembly is shown with respect to member or housing 320, in certain embodiments both housings include bellows assemblies to isolate their respective valves during connection.

Figure 21A:
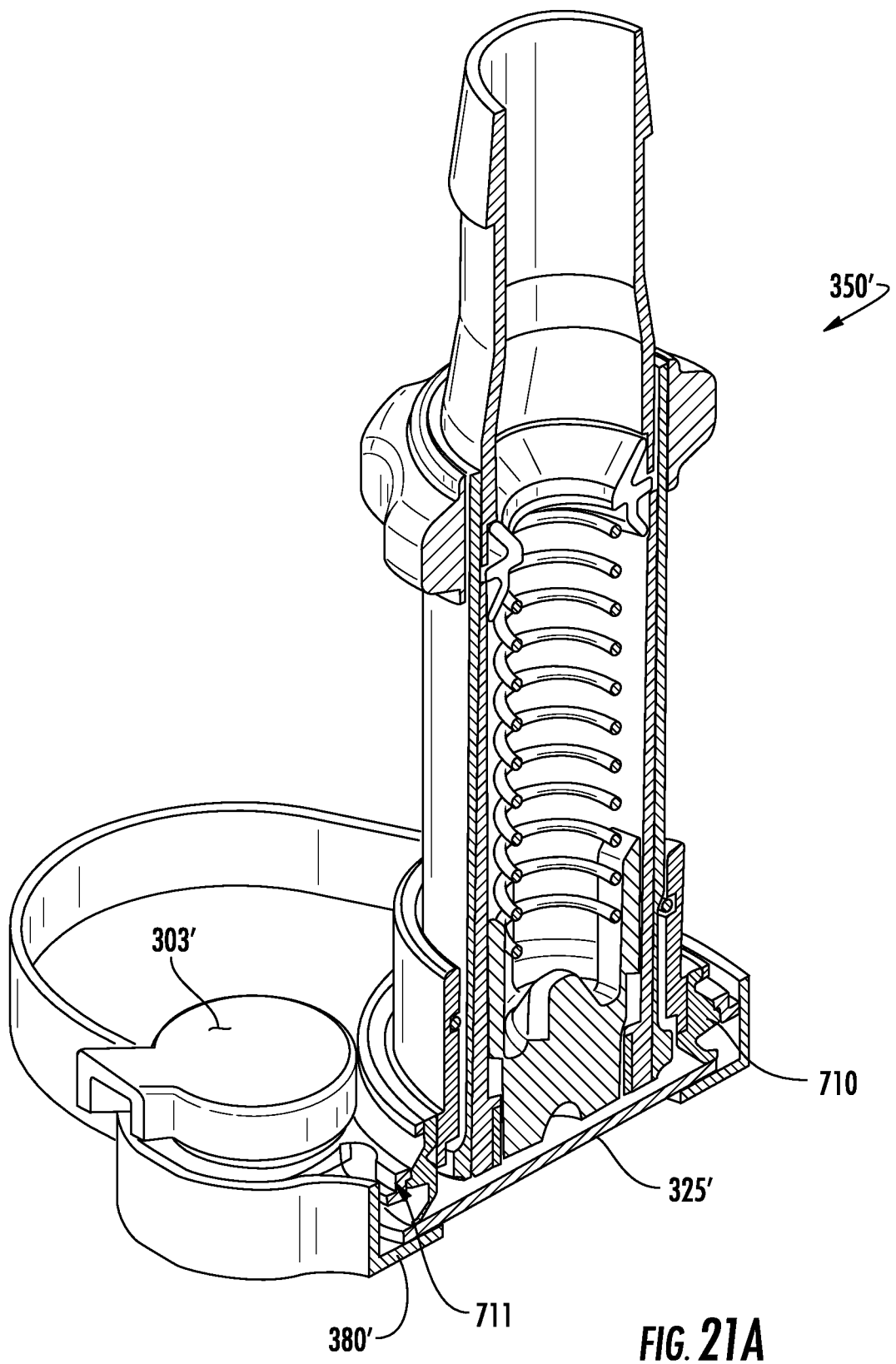
FIG. 21A is a perspective view, in partial cross-section, of one housing of a fluid transfer device in the closed position in accordance with certain embodiments.
Figure 21B:
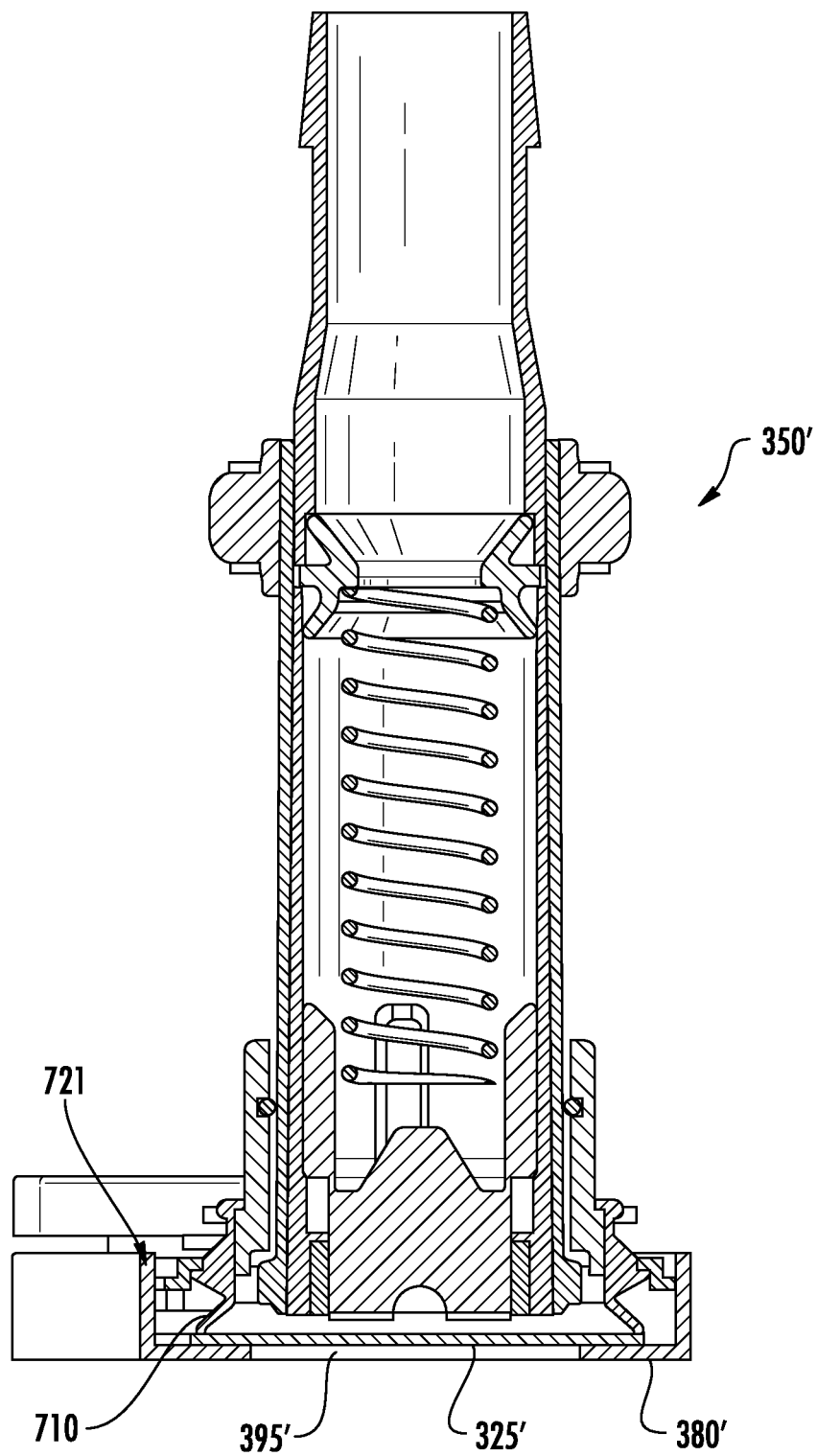
FIG. 21B is cross-sectional view of the closed position of FIG. 21A.
Figure 22A:
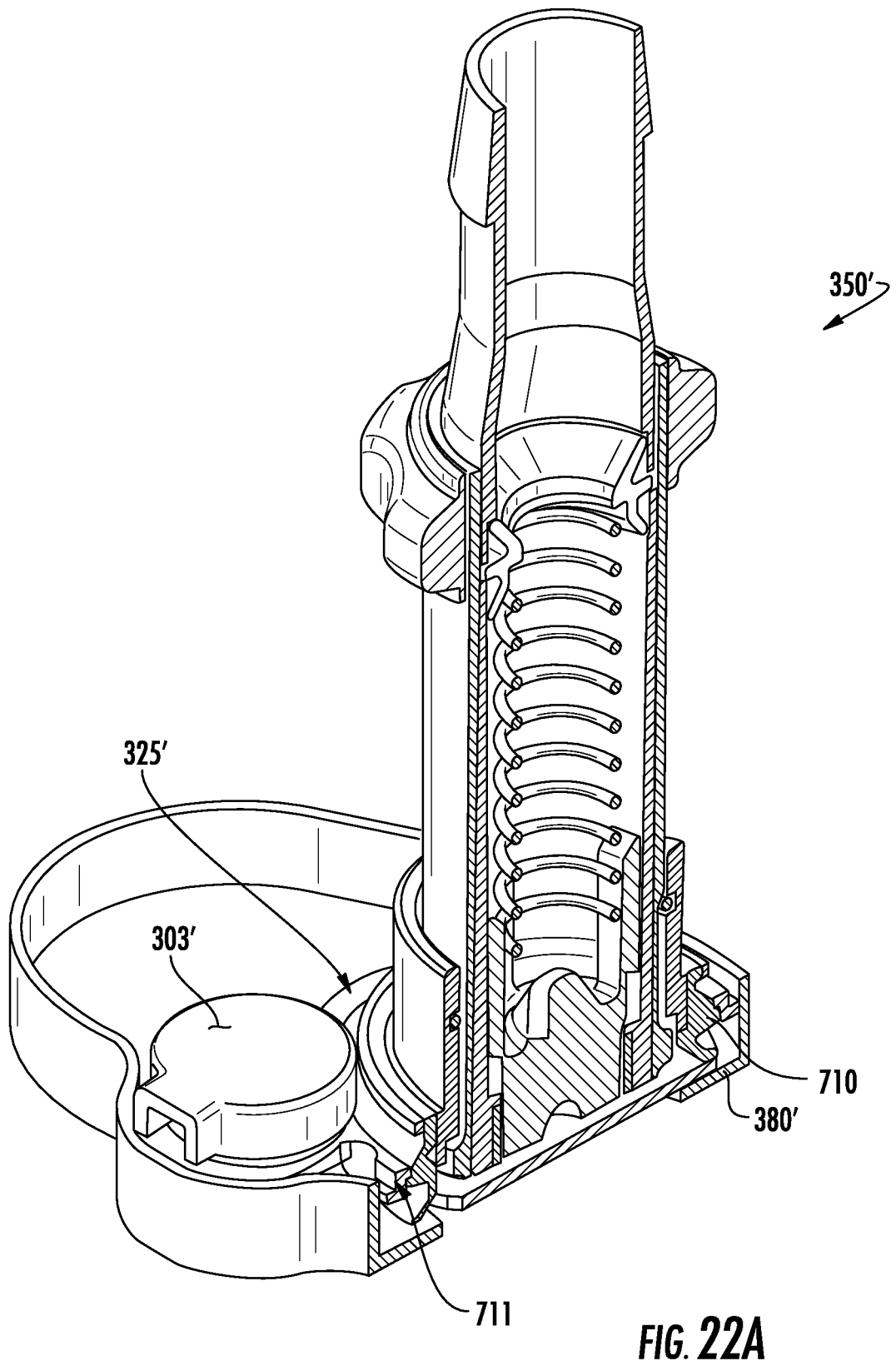
FIG. 22A is a perspective view, in partial cross-section, of one housing of a fluid transfer device in a partially open position in accordance with certain embodiments.
Figure 22B:
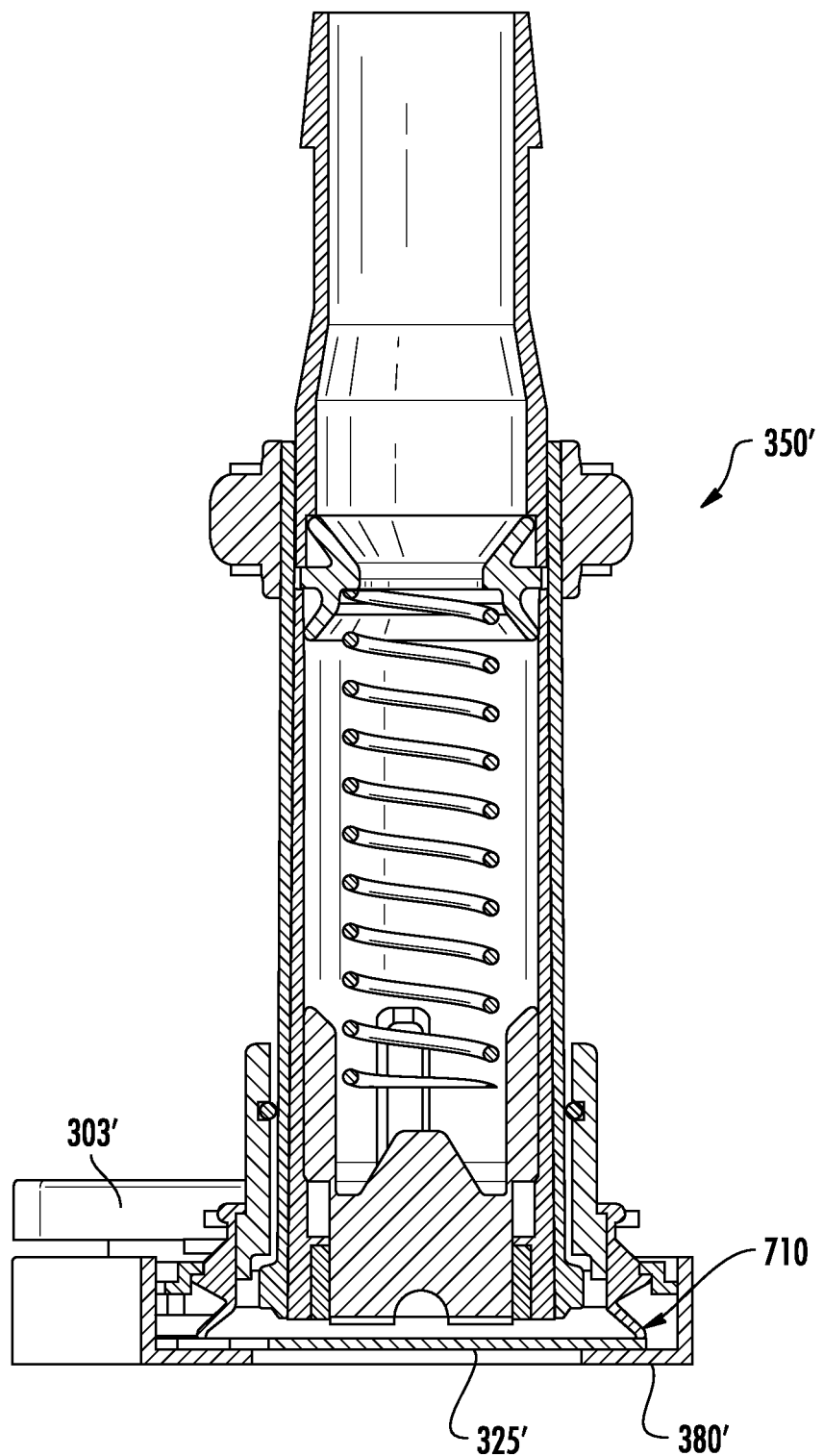
FIG. 22B is cross-sectional view of the partially opened position of FIG. 22A.
Figure 23A:
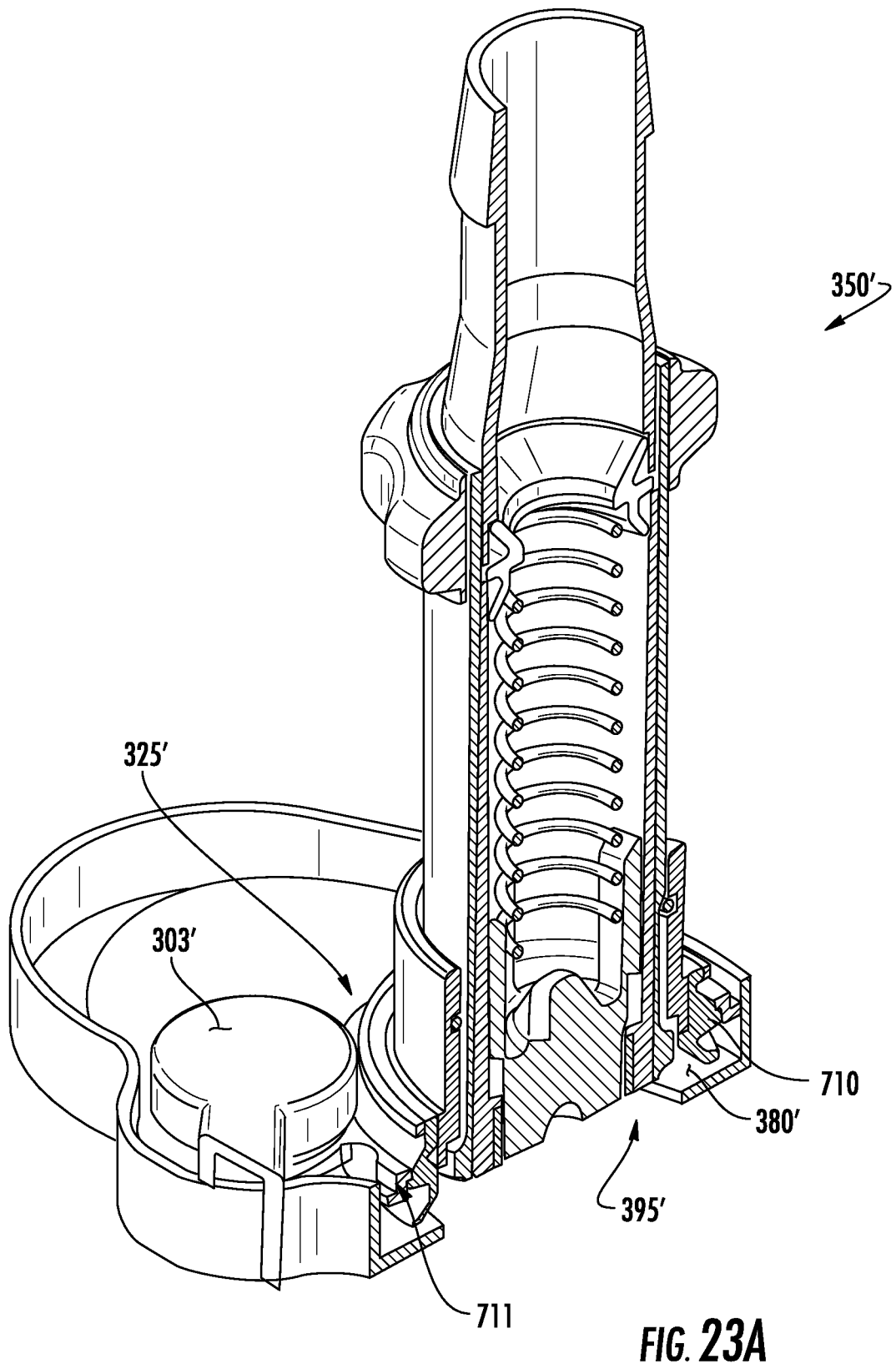
FIG. 23A is a perspective view, in partial cross-section, of one housing of a fluid transfer device in an almost fully open position in accordance with certain embodiments.
Figure 23B:
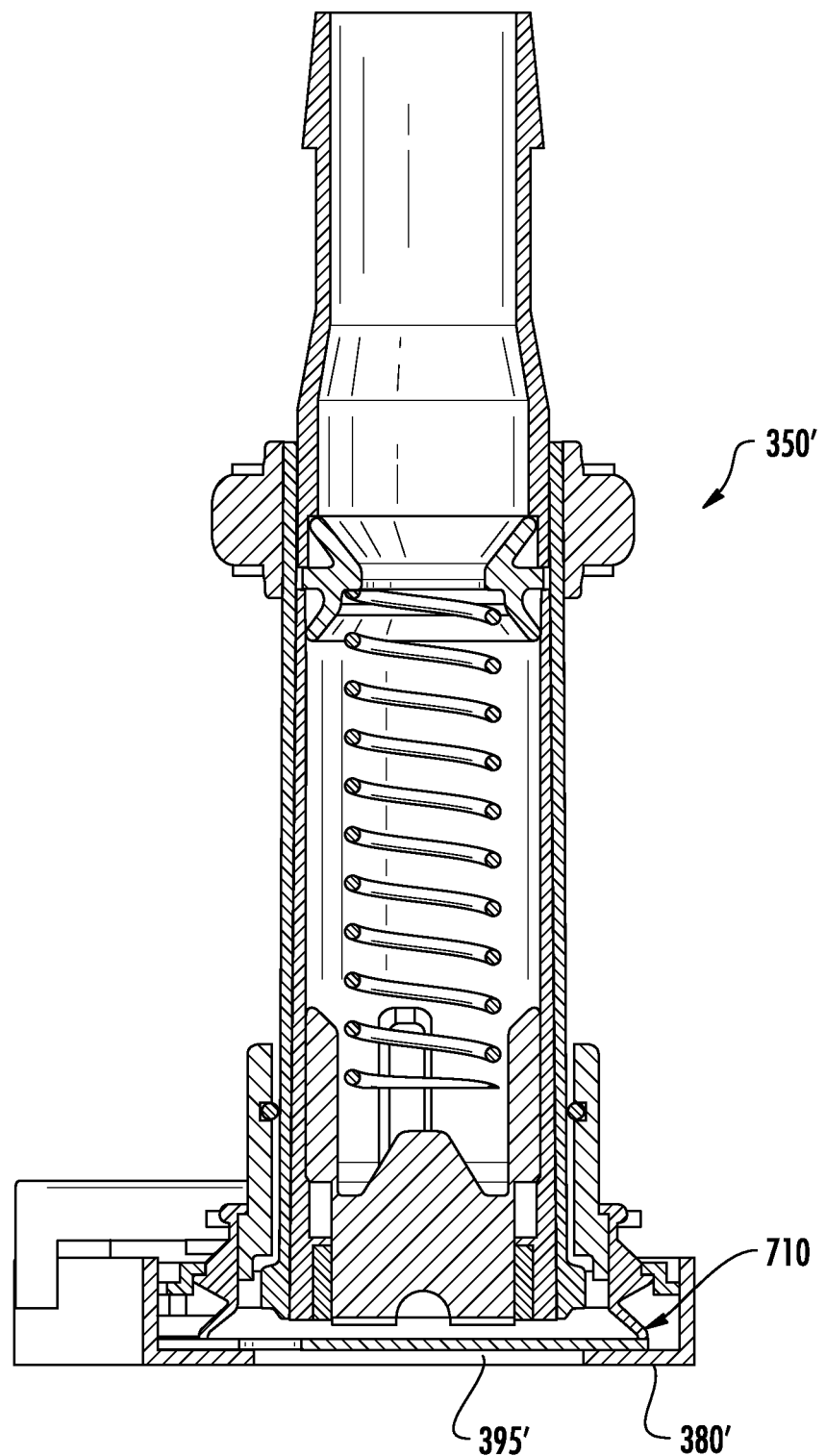
FIG. 23B is cross-sectional view of the almost fully opened position of FIG. 23A.
Figure 24A:
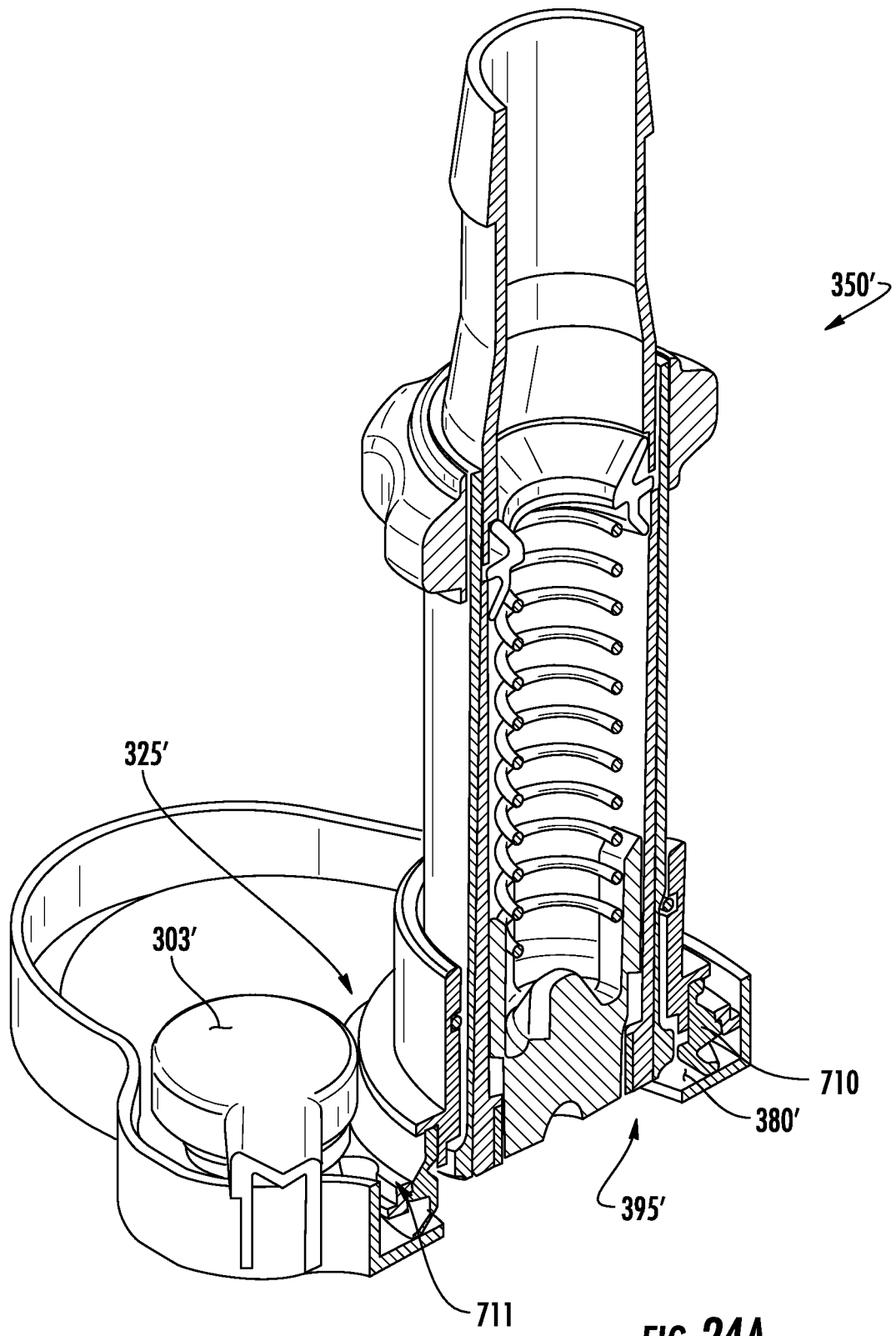
FIG. 24A is a perspective view, in partial cross-section, of one housing of a fluid transfer device in a fully open position in accordance with certain embodiments.
Figure 24B:
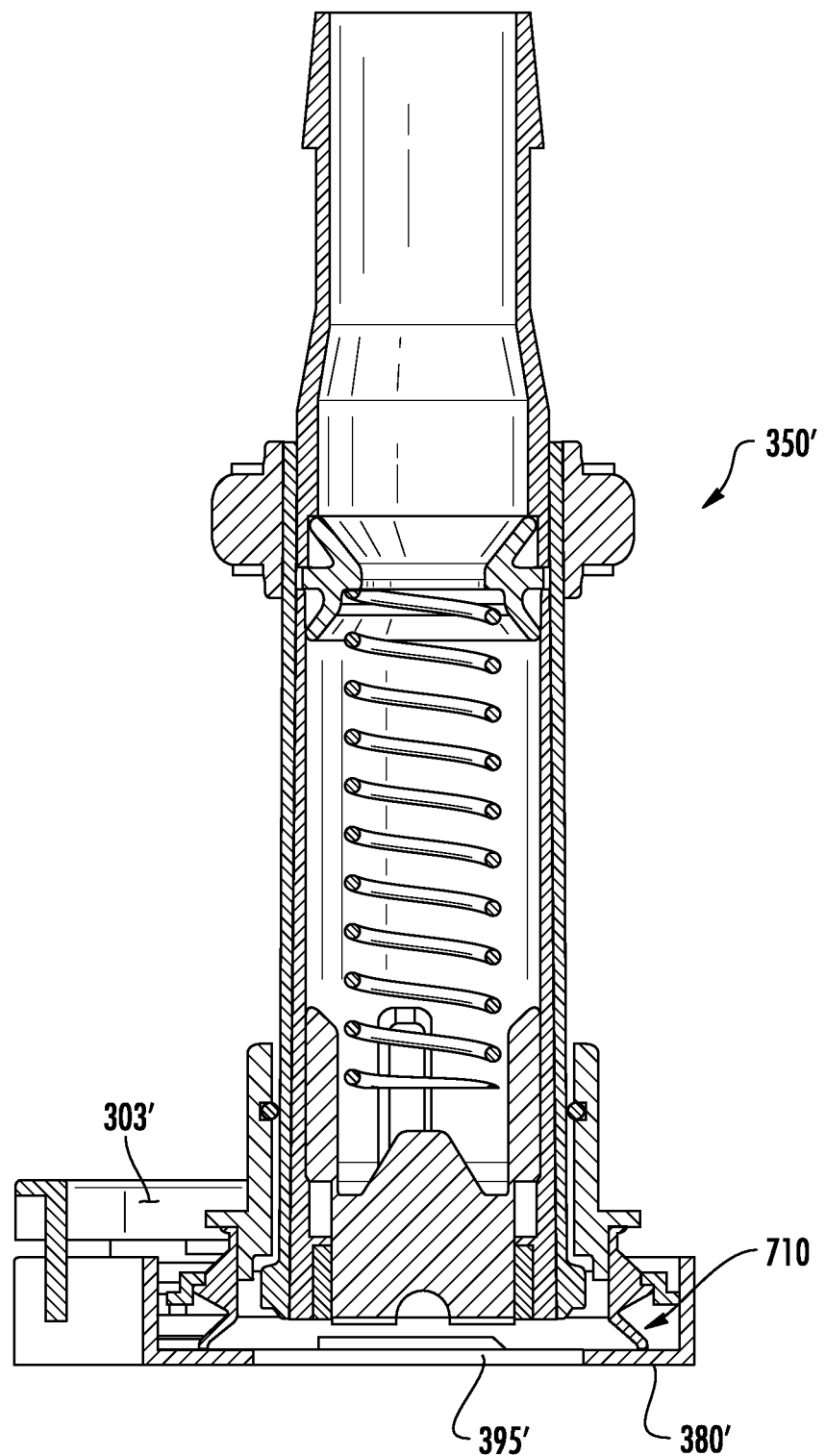
FIG. 24B is cross-sectional view of the fully opened position of FIG. 24A.

FIGS. 21A and 21B illustrate the fluid transfer device with the valve members in the closed position, i.e., the door 325' is positioned over the valve port with the bellows 710 against the door 325'. As seen in FIGS. 22A and 22B, as the first and second members or housings are twisted in opposite directions to lock them together, the door 325' begins to rotate to the open position. The bellows seal retainer member 711 also begins to rotate as the pins ride in the cam slot, and the bellow seal 710 breaks from the door 325'. As rotation continues as shown in FIGS. 23A and 23B, the door 325' rotates past the bellow seal 710. The pins in the seal retainer member 711 continue their travel in the cam slots to lower the bellows seal 710 towards the bottom plate 380'. The position of the door 325' and bellows 710 upon completion of the rotation is shown in FIGS. 24A and 25B. The door 325' is in the full open position, and the valve port 395' is unobstructed by the door. Similar door movement occurs at the same time in the other member or housing, allowing fluid communication between the two members or housings. The bellows 710 seals against the bottom plate 380' of the housing. The housings are now locked together, the valve ports open, and the valve members can be engaged by relative axially displacement of one into the other.

Figure 26:
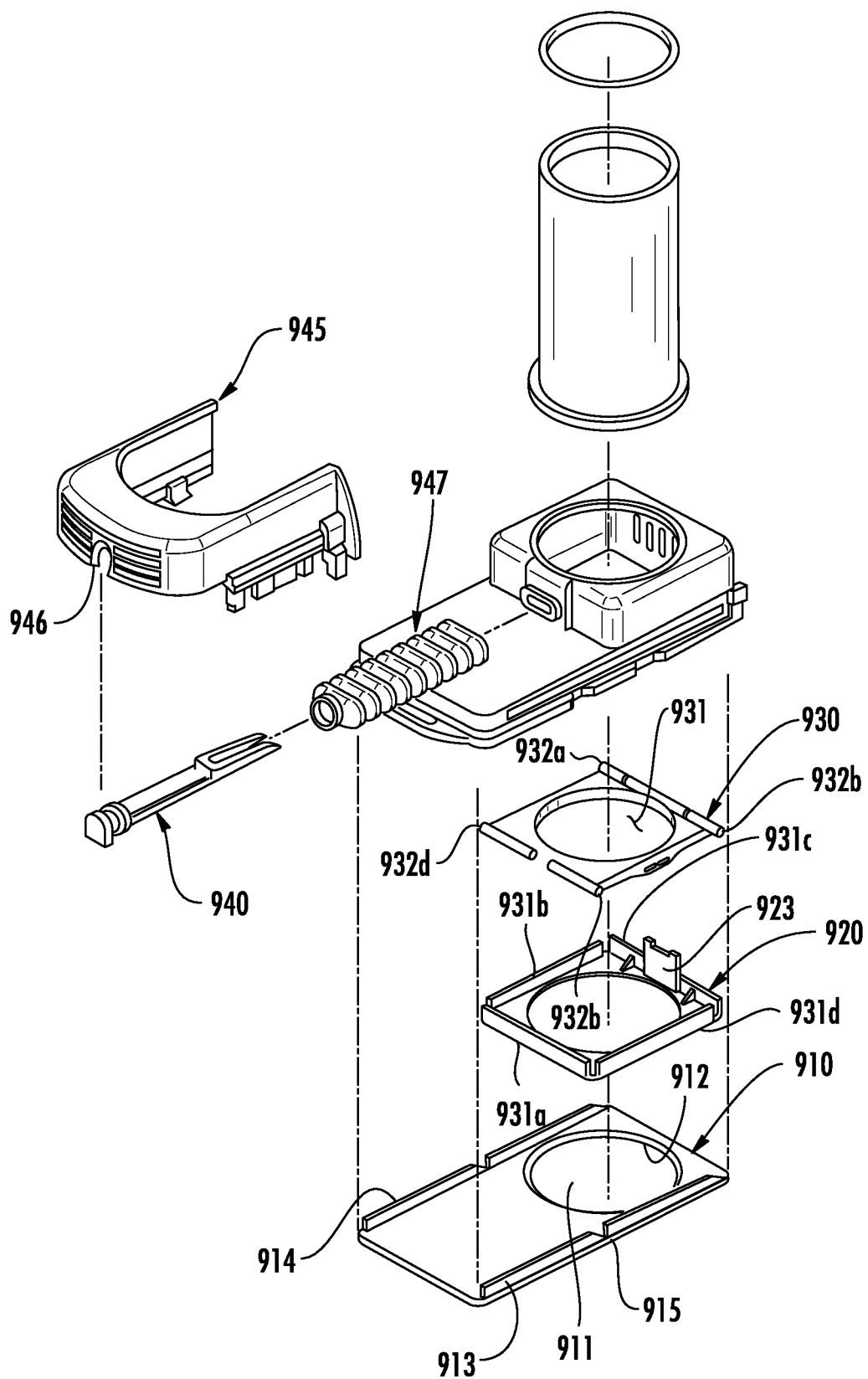
FIG. 26 is an exploded view of an alternative door assembly in accordance with certain embodiments.
Figure 26A:
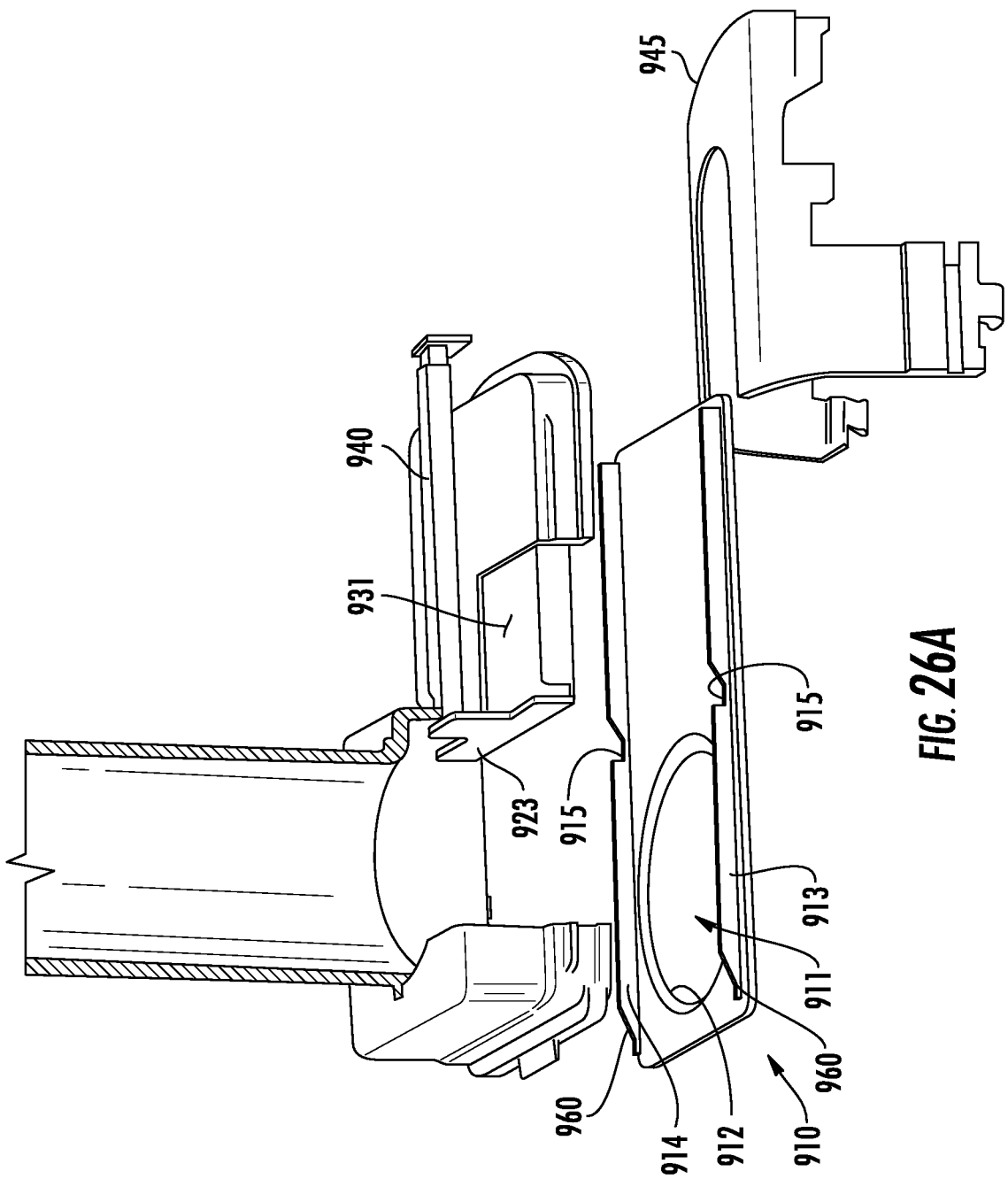
FIG. 26A is an exploded view of the alternative door assembly of FIG. 26 shown partially assembled.

FIG. 26 illustrates an alternative embodiment where the doors are brought in close proximity to one another in the closed position, thereby reducing or eliminating dead volume between them. In certain embodiments, each door assembly includes a face plate member 910 that includes an opening 911 that may have a gasket 912 fitted about its perimeter. The face plate member 910 includes a pair of opposite elongated side track members 913, 914 that extend upwardly from the surface of the face plate member 910. In certain embodiments, each track member 913, 914 includes an intermediate notch 915 which creates a cam for the plug pins 932a-d to push the door flush to the face upon closing and retracting when opening. Each track member 913, 914 also includes an end ramp 960 on which two of the plug pins ride when the door cams down to its closed position or up to its open position. The notches and ramps cooperate with mating track of cam 624 (FIG. 25), working together to trap the plug pins; one cam 624 bumps the door forward to close, and the mating rail on the cover bumps backward to open. In certain embodiments, each track 913, 914 is positioned slightly inwardly of a side edge of the face plate member 910 so that the region between each track member and the side edge forms, with a respective track member, an L-shaped track for the door assembly to ride on. In certain embodiments, a carrier member 920 is configured to carry plug 930, and includes four upwardly extending side walls 931a-d as shown. Carrier member 920 also includes upwardly extending notched tab 923 which recites slotted shaft 940 as shown in FIG. 26A. Plug 930 includes a solid downwardly projecting cylindrical portion 931 that is shaped to seal in opening 911 with the aid of gasket 912.

Figure 26C:
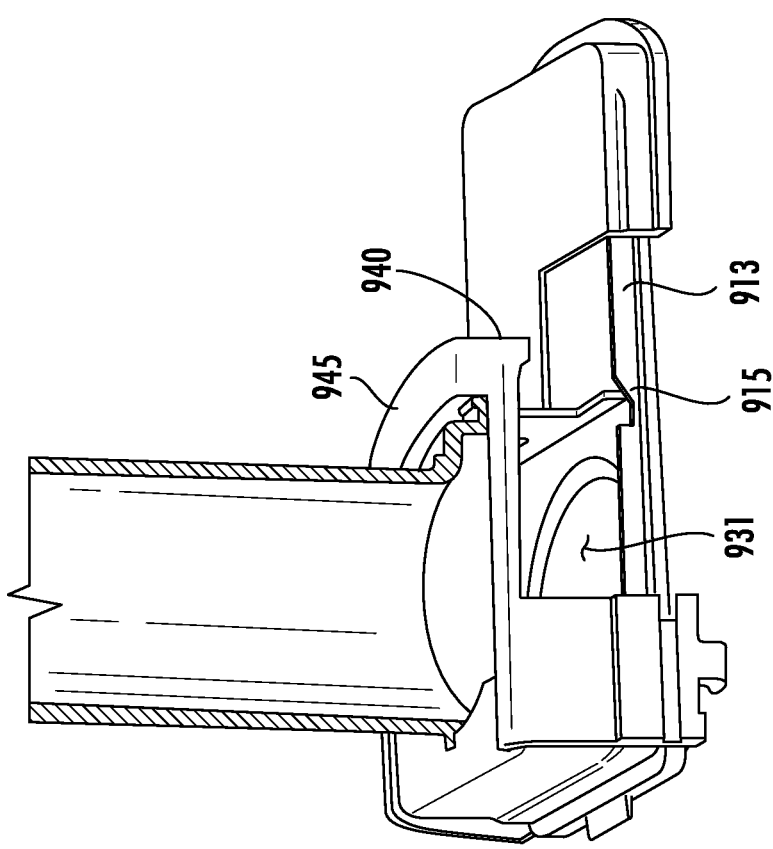
FIG. 26C is a perspective view of the alternative door assembly of FIG. 26 shown in the closed position.

As shown in FIG. 26B, handle 945 slides onto the housing and rides in the L-shaped track. A slot 946 (FIG. 26) in the end face of the handle 945 engages shaft 940. Bellows 947 may enclose shaft 940. Actuation of the handle 945 to the closed position translates the plug 931 from the open position to the closed position over the opening 911 in the member 910, as shown in FIG. 26C. The plug 931 is now flush to the face of the connector housing, reducing or eliminating dead volume trapped between it and the plug of the other housing member (which is similarly designed).

What is claimed is:
1. A fluid transfer device comprising:
    a first member, comprising a first body member having a first valve port, a first door actuatable between a first valve port open position and a first valve port closed position, a first locking handle assembly and a first valve member;
    a second member, comprising a second body member having a second valve port, a second door actuatable between a second valve port open position and a second valve port closed position, a second locking handle assembly and a second valve member;
    said first member and said second member being pivotally connected such that said first and second members are engaged upon relative pivoting of said first member and said second member, and wherein actuation of said first and second locking handle assemblies locks said first member and second member together and actuates said first door to said first valve port open position and said second door to said second valve open position, thereby creating fluid communication between said first and second members;
    wherein said first door comprises a face plate member having an opening and a pair of opposite elongated side track members that extend upwardly from said face plate member, each elongated side track member having an intermediate notch and an end ramp; and
    a plug having a cylindrical portion shaped to seal said opening in said face plate and having first and second plug pins on opposites sides of said plug, said first plug pins cooperating with said intermediate notch and said second plug pins cooperating with said end ramp during opening and closing of said door.

2. The fluid transfer device of claim 1, wherein said second door comprises a second face plate member having an opening and a pair of opposite elongated side track members that extend upwardly from said face plate member, each elongated side track member having an intermediate notch and an end ramp; a second plug having a cylindrical portion shaped to seal said opening in said face plate and having first and second plug pins on opposites sides of said plug, said first plug pins cooperating with said intermediate notch and said second plug pins cooperating with said end ramp during opening and closing of said second door.

3. The fluid transfer device of claim 1, wherein when said first and second doors are in the open positions, said first valve member is displaceable into said second valve member.

4. The fluid transfer device of claim 1, wherein said first member comprises a vent.

5. The fluid transfer device of claim 4, wherein said vent comprises a membrane.

6. The fluid transfer device of claim 1, wherein said pair of opposite elongated side track members define with said face plate member a pair of L-shaped tracks, and wherein said fluid transfer device further comprises a handle slidable in said L-shaped tracks.

7. The fluid transfer device of claim 1, wherein the face plate member comprises a gasket in said opening.

8. The fluid transfer device of claim 1, wherein the face plate member comprises a perimeter gasket in said opening.

9. The fluid transfer device of claim 2, wherein the second face plate member comprises a gasket in said opening.

10. The fluid transfer device of claim 2, wherein the second face plate member comprises a perimeter gasket in said opening.

11. The fluid transfer device of claim 1, wherein said first member comprises a vent cover.

12. The fluid transfer device of claim 1, wherein the intermediate notch creates a cam for the plug pins to push the door flush to the face plate upon closing and retracting upon opening and wherein dead volume between said first door and said second door is reduced or eliminated.

13. The fluid transfer device of claim 1, further comprising a carrier member for carrying said plug.

14. The fluid transfer device of claim 1, further comprising an upwardly extending notched tab which receives a slotted shaft.

15. The fluid transfer device of claim 1, further comprising a slot in an end face of the first locking handle and engages a slotted shaft.

16. The fluid transfer device of claim 14, further comprising a bellows that encloses the slotted shaft.

* * * * *